US011998387B2

(12) United States Patent
Fredrick et al.

(10) Patent No.: US 11,998,387 B2
(45) Date of Patent: Jun. 4, 2024

(54) MULTILAYER HOUSING SEALS FOR ULTRASOUND TRANSDUCERS

(71) Applicant: Exo Imaging, Inc., Redwood City, CA (US)

(72) Inventors: Daniela Marisa Fredrick, Auburn, CA (US); Charles Baumgartner, Niskayuna, NY (US); Robert Laduca, Dublin, CA (US)

(73) Assignee: Exo Imaging, Inc., Santa Clara, CA (US)

( * ) Notice: Subject to any disclaimer, the term of this patent is extended or adjusted under 35 U.S.C. 154(b) by 45 days.

(21) Appl. No.: 17/574,265

(22) Filed: Jan. 12, 2022

(65) Prior Publication Data
US 2023/0218271 A1    Jul. 13, 2023

(51) Int. Cl.
*A61B 8/00* (2006.01)
(52) U.S. Cl.
CPC ........ *A61B 8/4444* (2013.01); *A61B 2562/18* (2013.01)
(58) Field of Classification Search
CPC .................................................. B06B 1/0292
See application file for complete search history.

(56) References Cited

U.S. PATENT DOCUMENTS

| | | |
|---|---|---|
| 4,511,052 A | 4/1985 | Klein et al. |
| 5,127,410 A | 7/1992 | King et al. |
| 5,810,733 A | 9/1998 | Van Creveld et al. |
| 6,958,255 B2 | 10/2005 | Khuri-Yakub et al. |
| 8,988,971 B2 | 3/2015 | Mueller et al. |
| 2003/0235119 A1 | 12/2003 | Wien et al. |
| 2005/0165312 A1* | 7/2005 | Knowles .............. G10K 11/02 600/459 |
| 2007/0239001 A1 | 10/2007 | Mehi et al. |

(Continued)

FOREIGN PATENT DOCUMENTS

| CN | 106536067 A | 3/2017 |
|---|---|---|
| CN | 107768335 A | 3/2018 |

(Continued)

OTHER PUBLICATIONS

PCT/US2022/012126 International Search Report and Written Opinion dated Apr. 1, 2022.

(Continued)

*Primary Examiner* — Colin T. Sakamoto
*Assistant Examiner* — Tommy T Ly
(74) *Attorney, Agent, or Firm* — Morgan, Lewis & Bockius LLP

(57) ABSTRACT

Described are systems, devices, and methods useful in the prevention and/or detection of liquid intrusion into ultrasound equipment. Ultrasound transducers and associated ultrasound circuitry, which can be located in an interior of an ultrasound system or device can be adversely affected by exposure to liquids. As described herein, ultrasound systems and devices can comprise a multilayer seal, for example, wherein the multilayer seal comprises one or more layers for preventing liquid intrusion and one or more layers for detection of liquid intrusion (e.g., wherein the one or more layers for detection of liquid intrusion comprise an indicator material capable of changing color when exposed to a liquid).

42 Claims, 11 Drawing Sheets

(56) References Cited

U.S. PATENT DOCUMENTS

| | | |
|---|---|---|
| 2007/0299345 A1 | 12/2007 | Adachi et al. |
| 2008/0296708 A1 | 12/2008 | Wodnicki et al. |
| 2009/0122651 A1 | 5/2009 | Kupnik et al. |
| 2010/0154547 A1* | 6/2010 | Fukada ................ B06B 1/0292 73/632 |
| 2010/0168583 A1 | 7/2010 | Dausch et al. |
| 2010/0292575 A1* | 11/2010 | Sharp ...................... A61B 8/00 600/459 |
| 2012/0277639 A1 | 11/2012 | Pollock et al. |
| 2013/0020698 A1 | 1/2013 | Hsieh et al. |
| 2013/0345567 A1 | 12/2013 | Sudol et al. |
| 2014/0184027 A1 | 7/2014 | Rice et al. |
| 2014/0187962 A1 | 7/2014 | Reiter |
| 2015/0061465 A1 | 3/2015 | Lee et al. |
| 2015/0087991 A1 | 3/2015 | Chen et al. |
| 2015/0097468 A1 | 4/2015 | Hajati et al. |
| 2015/0119717 A1* | 4/2015 | Yoshida ............... A61B 8/4494 600/447 |
| 2015/0282783 A1 | 10/2015 | Katsura et al. |
| 2016/0009544 A1 | 1/2016 | Rothberg et al. |
| 2016/0187301 A1 | 6/2016 | Gu |
| 2018/0003678 A1 | 1/2018 | Rothberg et al. |
| 2019/0015072 A1 | 1/2019 | Deladi et al. |
| 2019/0178849 A1 | 6/2019 | Abraham et al. |
| 2021/0086231 A1 | 3/2021 | Bircumshaw et al. |
| 2021/0088655 A1 | 3/2021 | Bircumshaw et al. |
| 2021/0094070 A1 | 4/2021 | Bircumshaw et al. |
| 2021/0153844 A1 | 5/2021 | Fredrick et al. |
| 2023/0124828 A1* | 4/2023 | Morimoto ............... G10K 11/04 310/334 |
| 2023/0208126 A1* | 6/2023 | Suenaga ................ H02G 15/06 250/515.1 |

FOREIGN PATENT DOCUMENTS

| | | |
|---|---|---|
| JP | 2004130138 A | 4/2004 |
| JP | 2018029147 A | 2/2018 |
| KR | 20160018235 A | 2/2016 |
| KR | 20170030605 A | 3/2017 |
| WO | WO-2008137030 A1 | 11/2008 |
| WO | WO-2016011000 A1 | 1/2016 |
| WO | WO-2017143307 A1 | 8/2017 |
| WO | WO-2019222116 A1 | 11/2019 |
| WO | WO-2019222118 A1 | 11/2019 |
| WO | WO-2020198257 A1 | 10/2020 |
| WO | WO-2021102127 A1 | 5/2021 |

OTHER PUBLICATIONS

PCT/US2022/021556 International Search Report and Written Opinion dated Jul. 22, 2022.
PCT/US2022/021556 Invitation to Pay Additional Fees dated May 26, 2022.
Mahn et al. Au—Sn solid-liquid interdiffusion (SLID) bonding for piezoelectric ultrasonic transducers. 2016 IEEE International Ultrasonics Symposium (IUS) Tours (pp. 1-4) (2016).
PCT/US2019/032060 International Search Report and Written Opinion dated Jul. 26, 2019.
PCT/US2019/032062 International Search Report and Written Opinion dated Jul. 29, 2019.
PCT/US2020/061261 International Search Report and Written Opinion dated Feb. 9, 2021.
PCT/US2021/056026 International Search Report and Written Opinion dated Jan. 28, 2022.
PCT/US2021/056669 International Search Report and Written Opinion dated Jan. 28, 2022.

* cited by examiner

MULTILAYER HOUSING SEALS FOR ULTRASOUND TRANSDUCERS

BACKGROUND

Disinfection of ultrasound equipment is extremely important for minimizing risk to patients and for maintaining a clean environment in which the equipment is used. In particular, it is important to thoroughly clean the exterior surfaces of the ultrasound probe head to reduce or eliminate microbial load. Some existing strategies for disinfection of ultrasound equipment involves exposing the exterior surfaces of the equipment to ultraviolet light. However, prolonged and/or repeated exposure to ultraviolet (UV) light can render plastic materials, which are often used in fabrication of ultrasound probe housings, brittle and can decrease the lifespan of the ultrasound equipment. Furthermore, UV light is limited to line-of-sight efficacy, which can complicate efforts to fully disinfect all surfaces of an ultrasound system component. In some cases, a liquid-based disinfectant can be used to reduce microbial load on ultrasound equipment. In many cases, it can be necessary to soak one or more ultrasound system components, including the ultrasound transducer head, in a liquid disinfectant to achieve thorough disinfection of the components' surface(s). Exposing ultrasound equipment to liquid disinfectants repeatedly or for extended periods of time (e.g., soaking ultrasound equipment in liquid-based disinfectants) can be detrimental to the continued functioning of equipment. Accordingly, improved ultrasound devices and systems are needed to facilitate thorough disinfection of ultrasound equipment surfaces while decreasing the risk of damage to the equipment.

SUMMARY

The sensitive components of ultrasound transducer heads can be at risk of damage if the transducer head housing is not sufficiently sealed against liquid intrusion. Liquid-based disinfectants and gels pose a significant risk to the internal components of ultrasound imaging devices, as they are applied to the ultrasound transducer head during and/or between uses of ultrasound systems. Of particular concern are high-level disinfectants, which can require extended contact with the transducer head, for instance, wherein the transducer head must be soaked in the disinfectant. Furthermore, the threat of liquid intrusion can be compounded by transducer head geometries and fabrication processes, which may complicate efforts to seal the outer shell of the transducer device.

Transducer devices and systems compromised by liquid intrusion can often suffer partial or complete failure, for example due to electrical short circuiting and/or physical interference of liquids with ultrasound waves transmission, propagation, or transduction within a component (e.g., a microelectromechanical system (MEMS)) of an ultrasound transducer. In some cases, partial or complete failure of all or a portion of the components of an ultrasound device from liquid intrusion can necessitate replacement of the ultrasound device, which can be extremely expensive. Thus, detection and/or prevention of liquid intrusion into ultrasound devices can be critical to the economic feasibility of ultrasound technology in many medical settings. Devices and systems described herein can be effective in reducing the risk of liquid intrusion into ultrasound transducer devices and facilitating the identification and/or repair of ultrasound equipment compromised by liquid intrusion.

In some aspects, an ultrasound device comprises: an outer barrier surrounding an ultrasound transducer, the outer barrier comprising: a lens, a housing, and a multilayer seal in contact with the lens and the housing, wherein the multilayer seal comprises a first layer and a second layer, the first layer comprising an indicator material and the second layer comprising a first sealant. In some cases, the multilayer seal further comprises a third layer, the third layer comprising a second sealant. In some cases, the first sealant has a higher viscosity than the second sealant. In some cases, the first sealant is a thixotropic material. In some cases, the first sealant is a silicone-based sealant. In some cases, the outer barrier is impermeable to liquids. In some cases, the second sealant is a silicone-based sealant. In some cases, the first sealant is an adhesive. In some cases, the second sealant is an adhesive. In some cases, the multilayer seal is disposed within a gap between the lens of the device and the housing of the device. In some cases, the multilayer seal is in contact with the entirety of a perimeter of the lens. In some cases, the multilayer seal is in contact with the entirety of a perimeter of an aperture of the housing. In some cases, the second layer is in contact with the housing and with the lens. In some cases, the second layer is in contact with the entirety of a perimeter of the lens. In some cases, the second layer is in contact with the entirety of a perimeter of an aperture of the housing. In some cases, the preceding claims, wherein the second layer is disposed proximal to the first layer relative to the ultrasound transducer. In some cases, the third layer is disposed distal to the first layer relative to the ultrasound transducer. In some cases, the third layer is in contact with the entirety of a perimeter of the lens. In some cases, the third layer is in contact with the entirety of a perimeter of an aperture of the housing. In some cases, the third layer is in contact with the entirety of a distal surface of the second layer. In some cases, an interface of a distal surface of the third layer and a distal surface of the lens is smooth. In some cases, an interface of a distal surface of the third layer and a distal surface of the lens is flat. In some cases, the indicator material comprises a material that undergoes a color change after contacting a liquid. In some cases, the indicator material changes from a first color to a second color when contacted with the liquid. In some cases, the liquid is a disinfectant. In some cases, the liquid comprises water. In some cases, the ultrasound transducer is coupled to a proximal surface of the lens. In some cases, the lens is an ultrasound acoustic lens. In some cases, the ultrasound transducer comprises a microelectromechanical system (MEMS) array. In some cases, the multilayer seal has a thickness from 1 μm to 1000 μm. In some cases, the multilayer seal has a thickness that is constant. In some cases, the multilayer seal has a thickness that is not constant. In some cases, the first layer has a thickness from 1 μm to 125 μm. In some cases, the first layer has a thickness from 1 μm to 100 μm. In some cases, the first layer has a thickness that is constant. In some cases, the first layer has a thickness that is not constant. In some cases, the second layer has a thickness from 100 μm to 1000 μm. In some cases, the second layer has a thickness less than 750 μm. In some cases, the second layer has a thickness that is constant. In some cases, the second layer has a thickness that is not constant. In some cases, the multilayer seal has a width from 100 μm to 1000 μm. In some cases, the second layer has a width that is constant. In some cases, the second layer has a width that is not constant. In some cases, the lens is coupled to the ultrasound transducer. In some cases, the indicator material comprises an adhesive. In some cases, the indicator material is adhered to a surface of the ultrasound transducer.

In some cases, the indicator material is adhered to a surface of an ASIC of the ultrasound device. In some cases, the indicator material is adhered to a surface of a MEMS wafer of the ultrasound device. In some cases, the indicator material is disposed between the second layer and the third layer.

In some aspects, a method of manufacturing an ultrasound device comprises: assembling a housing and a lens of to substantially surround an ultrasound transducer, wherein the lens is coupled to the ultrasound transducer; and applying a multilayer seal to fill a gap between the housing and the lens, wherein applying the multilayer seal comprises: applying a second layer of the multilayer seal to one or more interior surfaces of the gap such that the second layer contacts the entirety of a perimeter of the housing facing the gap and the entirety of a perimeter of the lens facing the gap, applying a first layer of the multilayer seal to a distal surface of the second layer, the first layer comprising an indicator material, and applying a third layer of the multilayer seal to a distal surface of the first layer, such that the third layer contacts the entirety of a perimeter of the housing facing the gap and the entirety of a perimeter of the lens facing the gap. In some aspects, a method of manufacturing an ultrasound device comprising: assembling a housing and a lens to substantially surround a plurality of internal components, the plurality of internal components comprising an ultrasound transducer coupled to the lens; and applying a multilayer seal to fill a gap between the housing and the lens, wherein applying the multilayer seal comprises: applying a first layer of the multilayer seal to a distal surface of one or more of the internal components, the first layer comprising an indicator material, and applying a second layer of the multilayer seal to one or more interior surfaces of the gap such that the second layer contacts the entirety of a perimeter of the housing facing the gap and the entirety of a perimeter of the lens facing the gap. In some cases, a method further comprises applying a third layer of the multilayer seal to a distal surface of the first layer, such that the third layer contacts the entirety of a perimeter of the housing facing the gap and the entirety of a perimeter of the lens facing the gap. In some cases, a method further comprises coupling the lens to the ultrasound transducer. In some cases, a method further comprises rendering a distal surface of the multilayer seal smooth at an interface of the third layer and the housing. In some cases, a method further comprises rendering a distal surface of the multilayer seal smooth at an interface of the third layer and the lens. In some cases, the second layer is thixotropic. In some cases, the third layer is self-leveling. In some cases, the second layer comprises a material with a higher viscosity than a material comprising the third layer. In some cases, the second layer is applied using a dispensing needle. In some cases, the indicator material undergoes a color change after contacting a liquid. In some cases, the liquid comprises a disinfectant. In some cases, the liquid comprises water. In some cases, the first layer has a thickness of no more than 150 micrometers. In some cases, the multilayer seal has a thickness of no more than 1,000 micrometers.

In some aspects, a method of detecting liquid intrusion in an ultrasound device comprises: contacting a distal surface of an outer barrier of the ultrasound device with a liquid, wherein the outer barrier comprises a multilayer seal disposed in a gap between a lens and a housing and coupled to the lens and the housing, wherein the multilayer seal comprises a first layer, and a second layer, the first layer comprising an indicator material and the second layer comprising a sealant; and observing a color change in the indicator material of the first layer. In some cases, the distal surface of the outer barrier is contacted with the liquid for 0.1 hours to 1 hour. In some cases, the liquid comprises water. In some cases, the liquid comprises a low-level disinfectant. In some cases, the distal surface of the outer barrier is contacted with the liquid for 1 hour to 24 hours. In some cases, the liquid comprises water. In some cases, the liquid comprises a high-level disinfectant. In some cases, a method further comprises replacing all or a portion of the outer barrier.

BRIEF DESCRIPTION OF THE DRAWINGS

A better understanding of the features and advantages of the present subject matter will be obtained by reference to the following detailed description that sets forth illustrative embodiments and the accompanying drawings of which.

DETAILED DESCRIPTION

Figure 1:
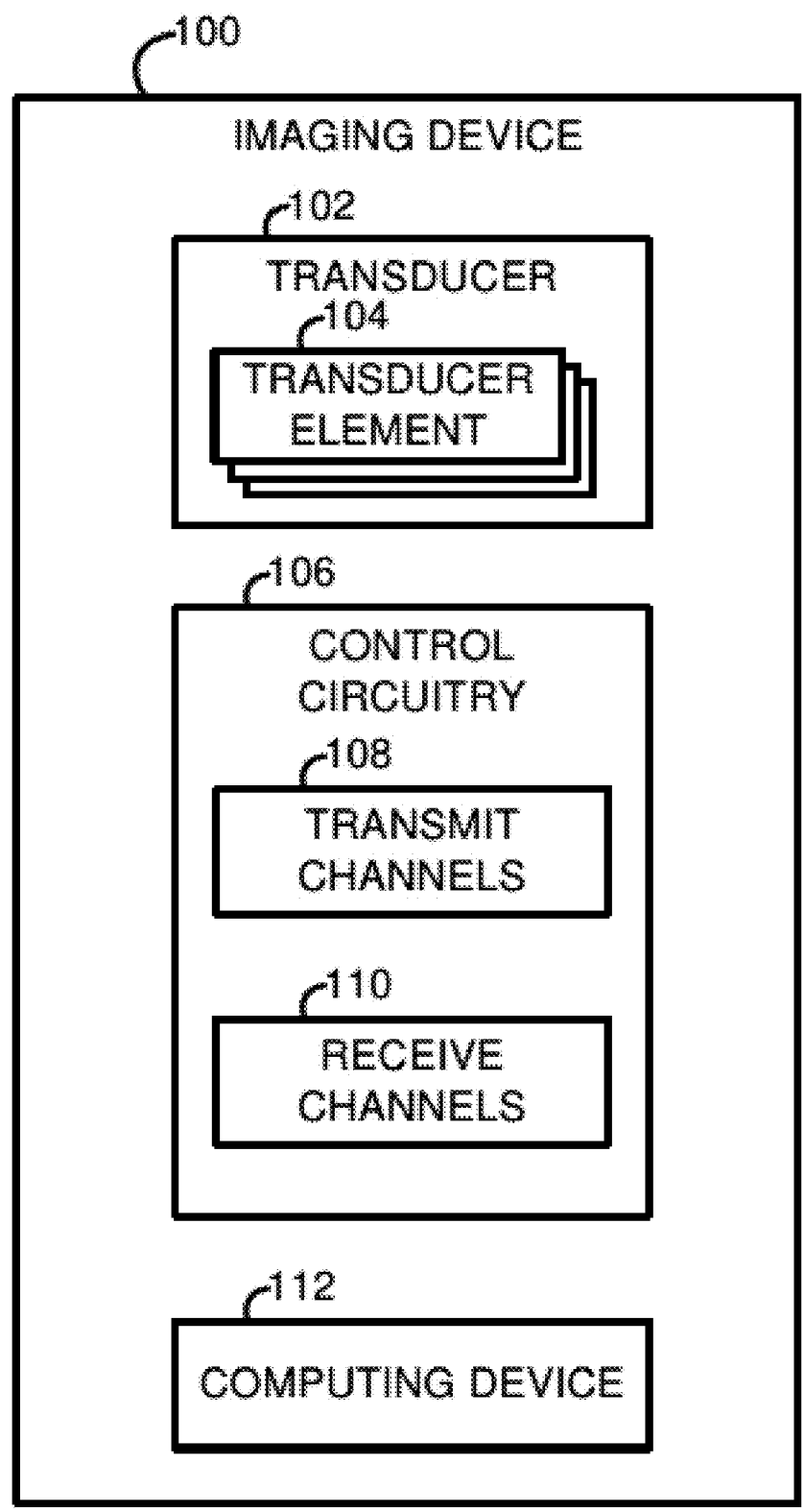
FIG. 1 shows a schematic diagram of an ultrasound device, in accordance with embodiments.
Figure 2:
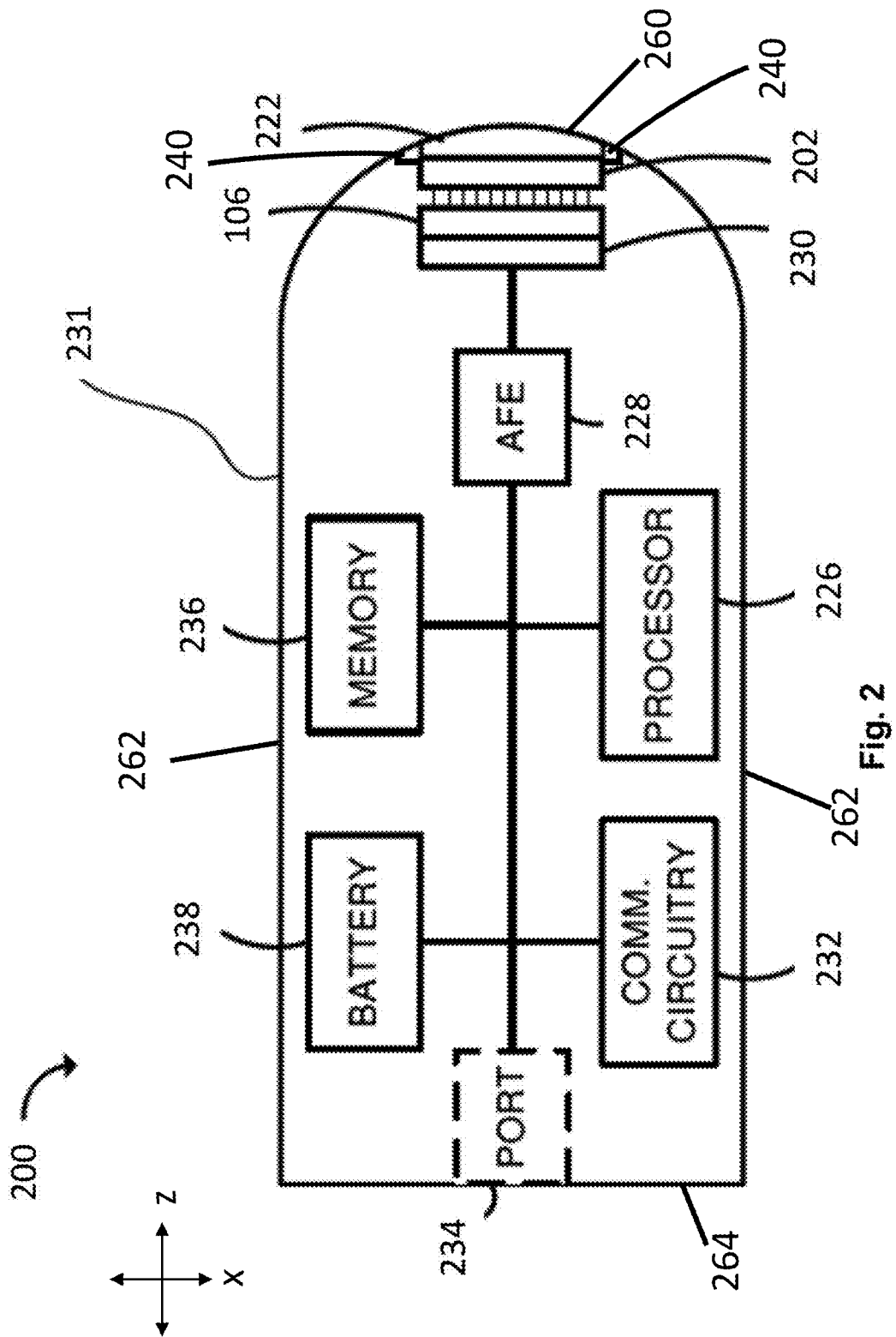
FIG. 2 shows a schematic diagram of an ultrasound device comprising a housing, a multilayer seal, and a lens, in accordance with embodiments.

Described herein are systems, devices, and methods for improved barrier function in ultrasound imaging applications. Ultrasound devices 100, 200 and systems are frequently brought into contact with liquids during use, and intrusion of such liquids into the interior of an ultrasound device can negatively affect the function of the device, potentially destroying sensitive electronic components (e.g., ultrasound transducers 102, 202 and/or associated electrical circuitry 106, for example, as shown in FIG. 1 and FIG. 2) located within a housing 231 of the device 100, 200. In addition to direct contact with ultrasound imaging media, such as acoustic gel, and/or bodily fluids, ultrasound devices and systems used in medical settings can require prolonged and/or repeated disinfection to protect patients from pathogens, which may be present on an outer surface of the ultrasound device. As described herein, ultrasound devices comprising a multilayer seal 240 can have increased protection against liquid intrusion, e.g., compared to devices and systems using some existing sealing technologies. In many cases, devices, systems, and methods disclosed herein can greatly improve the detection of liquid intrusion and/or a compromised liquid barrier of an ultrasound device or system. In some cases, detection of liquid intrusion and/or a compromised liquid barrier of an ultrasound device or system can reduce the risk that an ultrasound system or device malfunctioning from liquid intrusion is used to collect data in a medical setting. In some cases, detection of liquid intrusion and/or a compromised liquid barrier of an ultrasound device or system can enable the repair of the device or system before one or more components (e.g., an ultrasound transducer or electronic device) is damaged or destroyed.

Overview

An ultrasound system 100 or component thereof, for example an ultrasound device 200 such as an ultrasound probe, can comprise a multilayer seal 240. Ultrasound systems and devices comprising a multilayer seal 240 can have improved resistance to liquid intrusion. As shown in FIG. 2, an ultrasound system 100 can comprise an outer barrier. An outer barrier of an ultrasound system or device can be placed in contact with one or more liquids during or between uses, such as ultrasound acoustic gels, bodily fluids, and/or one or more disinfectants (e.g., liquid disinfectants). In many cases, an outer barrier of an ultrasound system or device can be a primary barrier to liquid intrusion into the interior of the ultrasound system or device. One or more components located in the interior an ultrasound system or device (e.g., an ultrasound transducer 202 (which can comprise a microelectromechanical system (MEMS) array), an application specific integrated circuit (ASIC), a printed circuit board, analog processing component(s) (e.g., analog front end 228 (AFE)), an electronic memory 236, a computer processor 226, a battery 238, communication circuitry 232, and/or a communication port 234) may be sensitive to exposure to liquids and can, in some cases, be damaged by liquid(s) that have breached the outer barrier. In many cases, a multilayer seal 240 can comprise a critical portion of an outer barrier of an ultrasound system or device. In some cases, an outer barrier comprising a multilayer seal 240 can reduce the likelihood (e.g., prevent) of damage to internal components (e.g., comprising an ultrasound transducer and/or an ASIC of the system or device), for example, as the result of liquid intrusion. In some cases, a multilayer seal 240 can improve ultrasound system or device maintenance and/or error diagnosis. For instance, a multilayer seal 240 can provide an indication (e.g., a visual indication) that a liquid (e.g., water or a disinfectant, such as a high-level disinfectant) has crossed the outer surface of an outer barrier and/or that liquid intrusion into the interior of an ultrasound system or device has occurred, in some cases.

Figure 3:
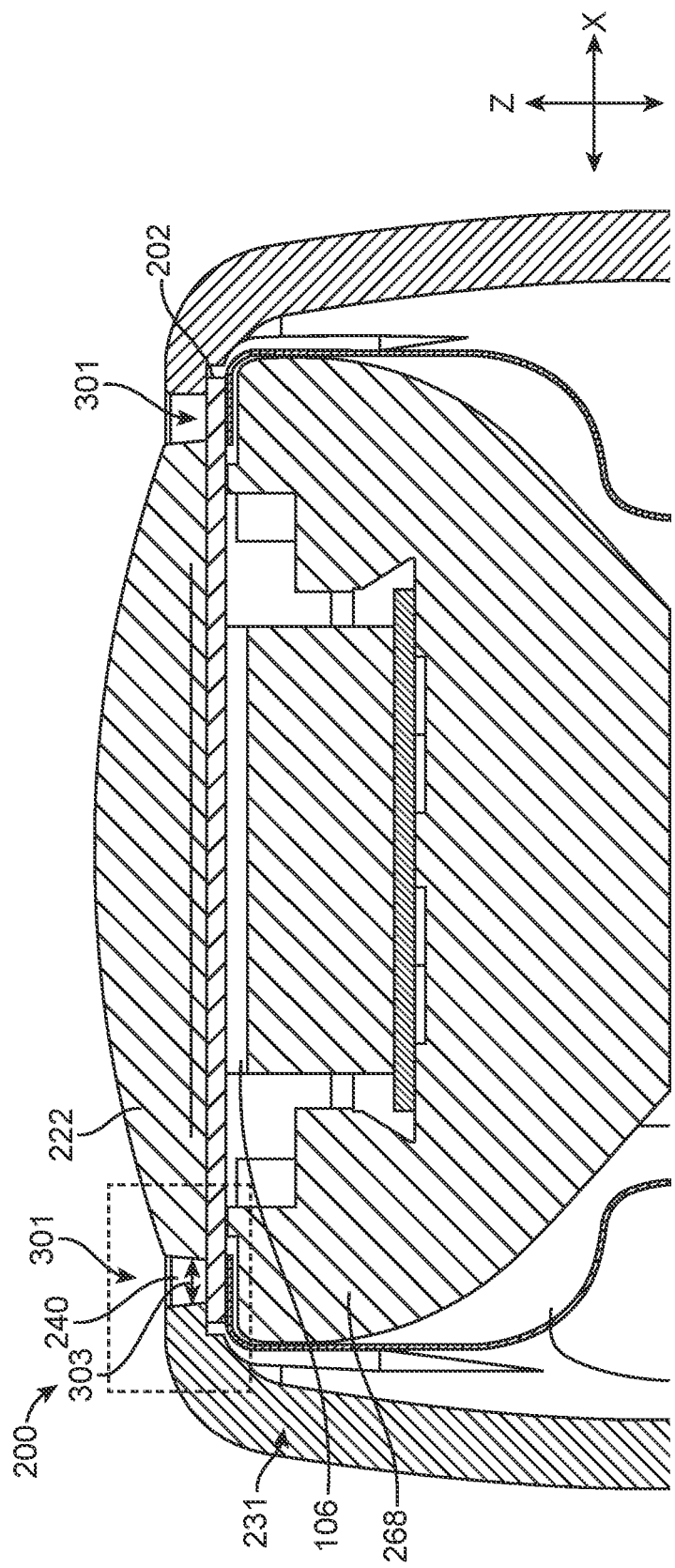
FIG. 3 shows a cross-sectional view of an ultrasound device comprising a housing, a multilayer seal, and a lens, in accordance with embodiments.
Figure 4:
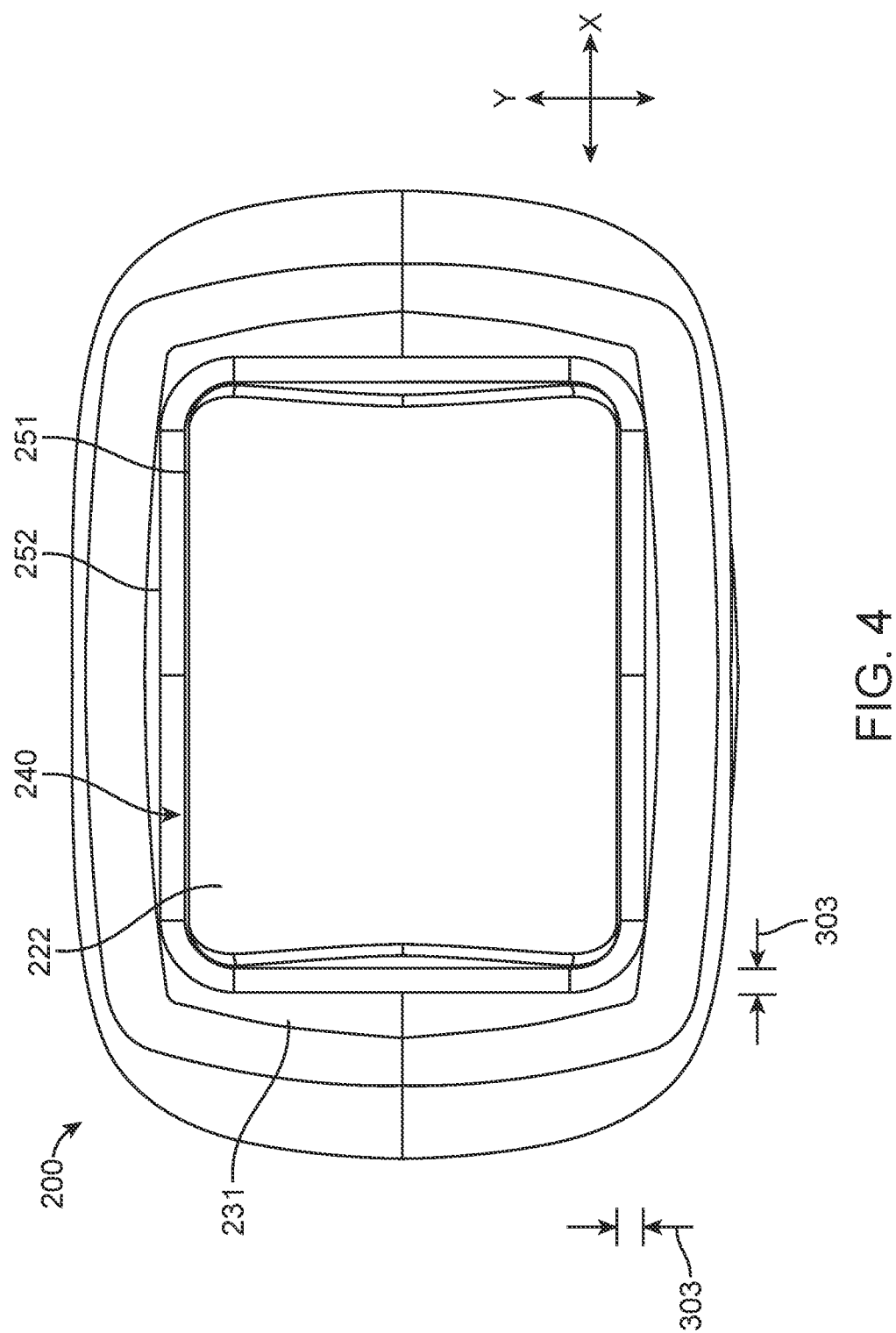
FIG. 4 shows a schematic of a distal end of an ultrasound device comprising a housing, a multilayer seal, and a lens, in accordance with embodiments.
Figure 5:
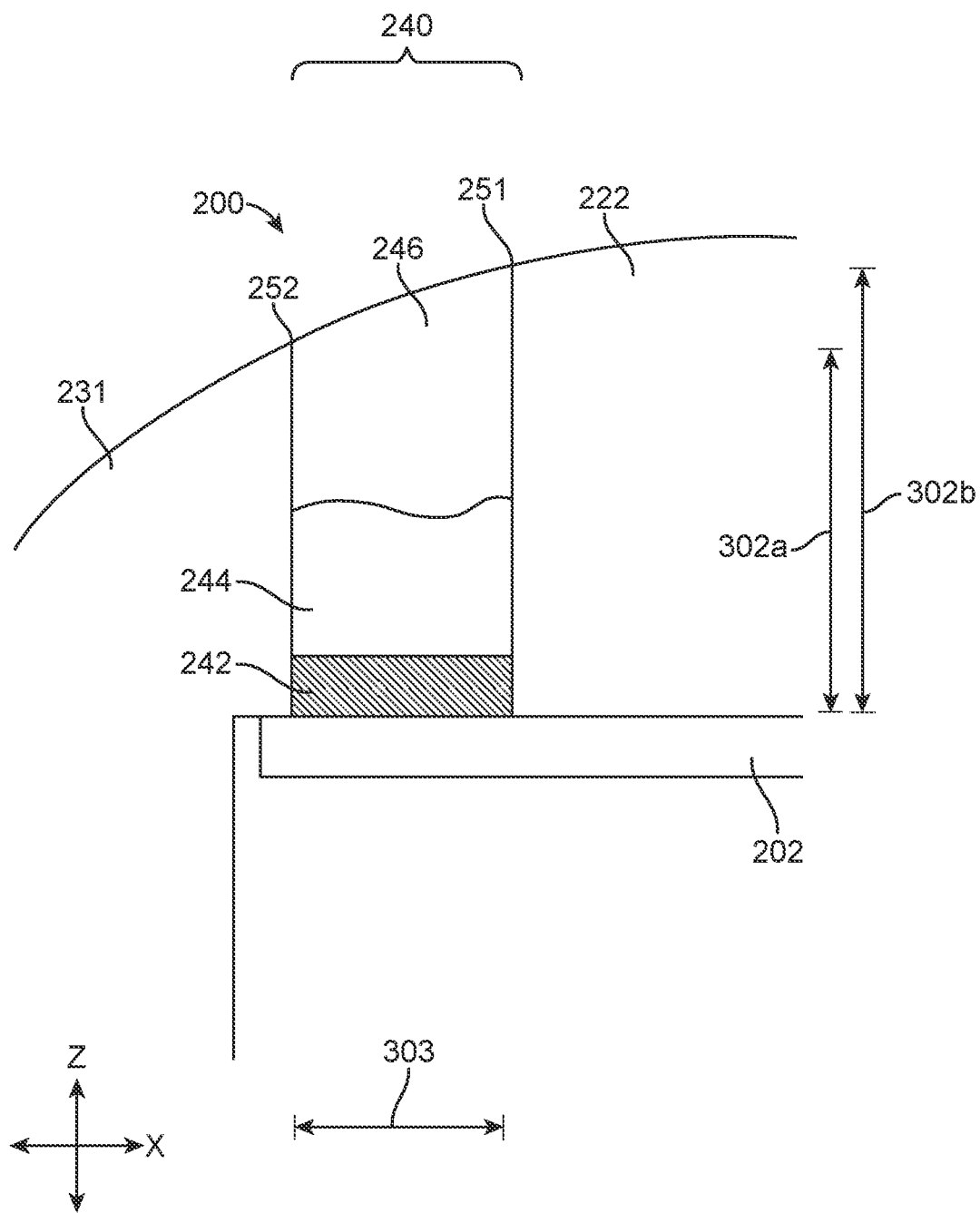
FIG. 5 shows a portion of an ultrasound device comprising a housing, a multilayer seal, and a lens, in accordance with embodiments.
Figure 6:
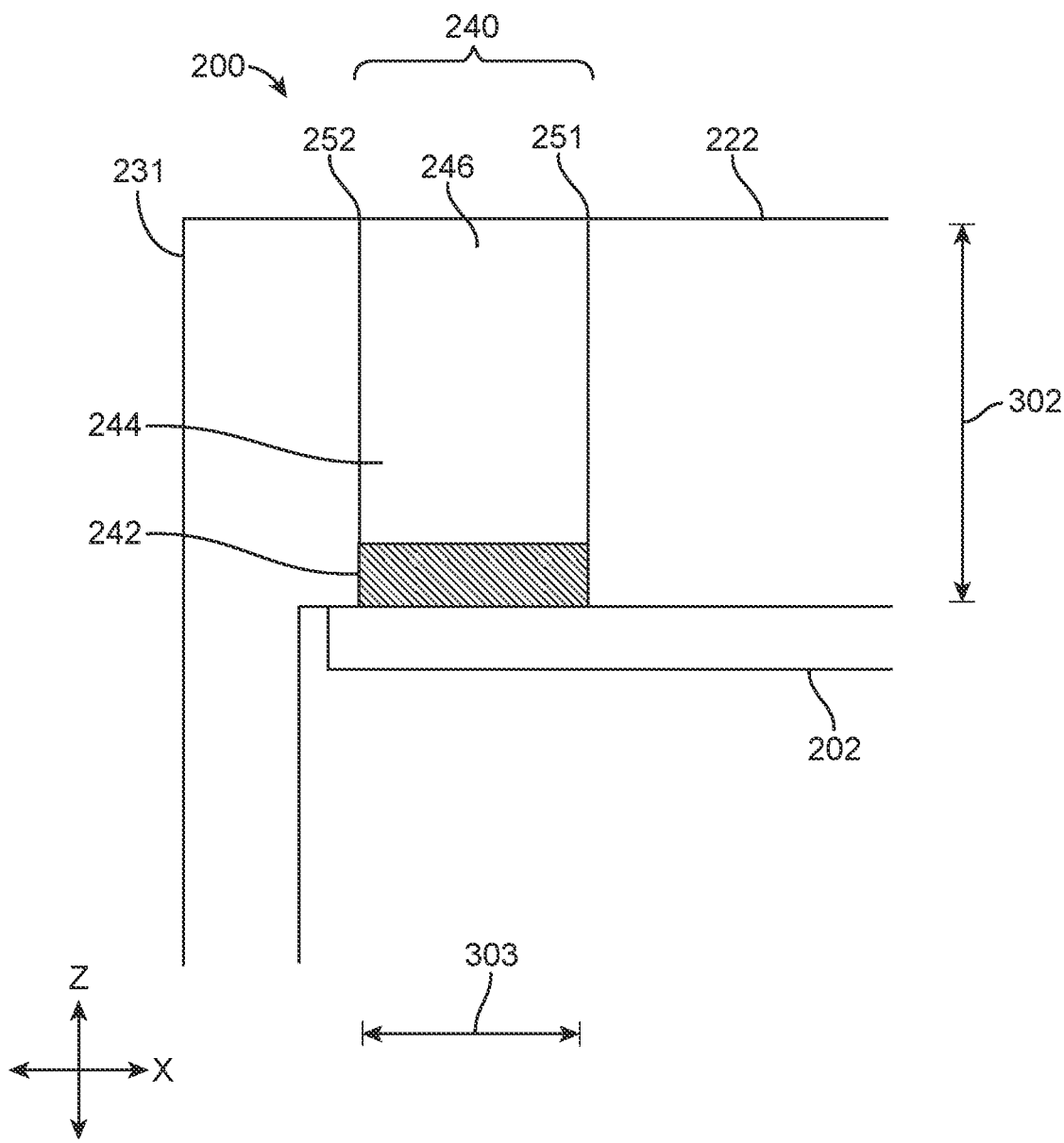
FIG. 6 shows a portion of an ultrasound device comprising a housing, a multilayer seal, and a lens, in accordance with embodiments.
Figure 7:
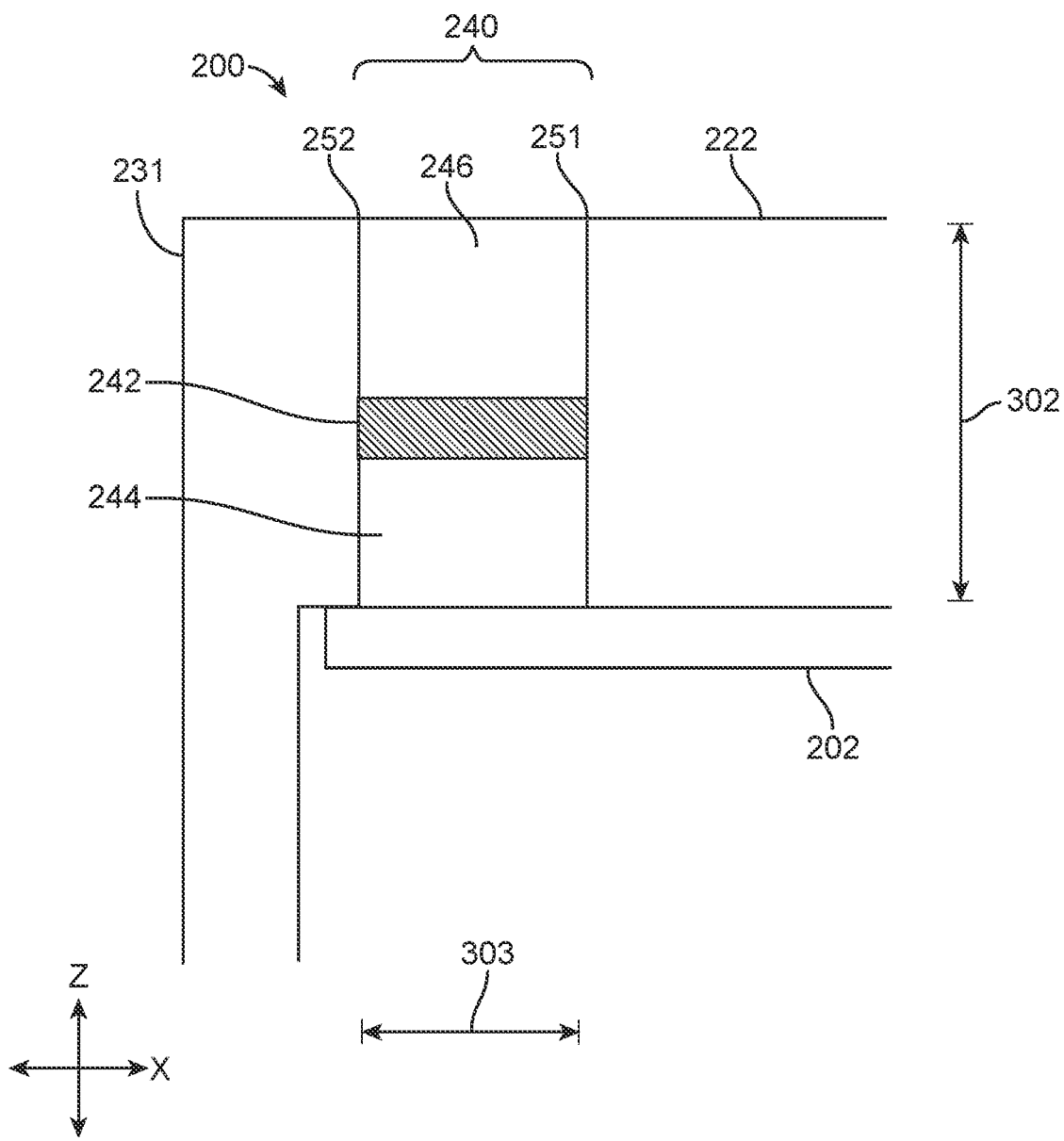
FIG. 7 shows a portion of an ultrasound device comprising a housing, a multilayer seal, and a lens, in accordance with embodiments.

An outer barrier of an ultrasound system component or device can comprise a multilayer seal 240. In some cases, an outer barrier of an ultrasound system or device can comprise a housing 231 and a lens 222 (e.g., wherein the lens optionally comprises a coating layer). In some cases, a multilayer seal 240 can be in contact with a housing 231 and a lens 222 of an ultrasound system 100 or device 200, for example, to establish a continuous outer barrier surrounding one or more internal components (e.g., including an ultrasound transducer 202) of an ultrasound system 100 or device 200. In some cases, a multilayer seal 240 can be in contact with an entirety of a perimeter (e.g., a circumferential perimeter) of a lens 222 (e.g., as shown in FIG. 4). In some cases, a multilayer seal 240 can be in contact with an entirety of a perimeter of a housing 231 (e.g., an inner perimeter of an aperture of a housing, e.g., as shown in FIG. 4). In some cases, a multilayer seal 240 can be disposed within a gap 301 between a lens 222 of an ultrasound device and a housing 231 of the ultrasound device, for example, as shown in FIG. 3. Some embodiments of a multilayer seal 240 disposed in a gap 301 of an ultrasound device can be seen in FIG. 5, FIG. 6, and FIG. 7, which are enlarged views of the region of FIG. 3 indicated by the dotted box. In some cases, a gap 301 of an ultrasound device or system can have a thickness 302 (e.g., in a z-direction, as shown in FIG. 5, FIG. 6, FIG. 7) of 1 micrometer (µm) to 1,000 micrometers. In some cases, a gap 301 of an ultrasound device or system can have a thickness 302 of 1 micrometer to 25 micrometers, 1 micrometer to 50 micrometers, 1 micrometer to 100 micrometers, 1 micrometer to 150 micrometers, 1 micrometer to 200 micrometers, 1 micrometer to 250 micrometers, 1 micrometer to 500 micrometers, 1 micrometer to 750 micrometers, 1 micrometer to 1,000 micrometers, 25 micrometers to 50 micrometers, 25 micrometers to 100 micrometers, 25 micrometers to 150 micrometers, 25 micrometers to 200 micrometers, 25 micrometers to 250 micrometers, 25 micrometers to 500 micrometers, 25 micrometers to 750 micrometers, 25 micrometers to 1,000 micrometers, 50 micrometers to 100 micrometers, 50 micrometers to 150 micrometers, 50 micrometers to 200 micrometers, 50 micrometers to 250 micrometers, 50 micrometers to 500 micrometers, 50 micrometers to 750 micrometers, 50 micrometers to 1,000 micrometers, 100 micrometers to 150 micrometers, 100 micrometers to 200 micrometers, 100 micrometers to 250 micrometers, 100 micrometers to 500 micrometers, 100 micrometers to 750 micrometers, 100 micrometers to 1,000 micrometers, 150 micrometers to 200 micrometers, 150 micrometers to 250 micrometers, 150 micrometers to 500 micrometers, 150 micrometers to 750 micrometers, 150 micrometers to 1,000 micrometers, 200 micrometers to 250 micrometers, 200 micrometers to 500 micrometers, 200 micrometers to 750 micrometers, 200 micrometers to 1,000 micrometers, 250 micrometers to 500 micrometers, 250 micrometers to 750 micrometers, 250 micrometers to 1,000 micrometers, 500 micrometers to 750 micrometers, 500 micrometers to 1,000 micrometers, or 750 micrometers to 1,000 micrometers. In some cases, a gap 301 of an ultrasound device or system can have a thickness 302 of 1 micrometer, 25 micrometers, 50 micrometers, 100 micrometers, 150 micrometers, 200 micrometers, 250 micrometers, 500 micrometers, 750 micrometers, or 1,000 micrometers. In some cases, a gap 301 of an ultrasound device or system can have a thickness 302 of at least 1 micrometer, 25 micrometers, 50 micrometers, 100 micrometers, 150 micrometers, 200 micrometers, 250 micrometers, 500 micrometers, 750 micrometers, or 1,000 micrometers. In some cases, a gap 301 of an ultrasound device or system can have a thickness 302 of at most 1 micrometer, 25 micrometers, 50 micrometers, 100 micrometers, 150 micrometers, 200 micrometers, 250 micrometers, 500 micrometers, 750 micrometers, or 1,000 micrometers. In some cases, a gap 301 of an ultrasound device or system can have a thickness 302 (e.g., in a z-direction, as shown in FIG. 5, FIG. 6, FIG. 7) of 1 micrometer (µm) to 2,000 micrometers. In some cases, a gap 301 of an ultrasound device or system can have a thickness 302 of 1 micrometer to 1,250 micrometers, 1 micrometer to 1,500 micrometers, 1 micrometer to 1,700 micrometers, 1 micrometer to 2,000 micrometers, 1,000 micrometer to 1,250 micrometers, 1,000 micrometer to 1,500 micrometers, 1,000 micrometer to 1,750 micrometers, 1,000 micrometer to 2,000 micrometers, 1,250 micrometers to 1,500 micrometers, 1,250 micrometers to 1,750 micrometers, 1,250 micrometers to 2,000 micrometers, 1,500 micrometers to 1,750 micrometers, 1,500 micrometers to 2,000 micrometers, or 1,750 micrometers to 2,000 micrometers. In some cases, a gap 301 of an ultrasound device or system can have a thickness 302 of 1,250 micrometers, 1,500 micrometers, 1,750 micrometers, or 2,000 micrometers. In some cases, a gap 301 of an ultrasound device or system can have a thickness 302 of at least 1,250 micrometers, 1,500 micrometers, 1,750 micrometers, or 2,000 micrometers. In some cases, a gap 301 of an ultrasound device or system can have a thickness 302 of at most 1 micrometer, 1,250 micrometers, 1,500 micrometers, 1,750 micrometers, or 2,000 micrometers. In some cases, a gap 301 of an ultrasound device or system can have a width 303 (e.g., in a x-direction or a y-direction, as shown in FIG. 4, FIG. 5, FIG. 6, FIG. 7) of 1 micrometer (μm) to 1,000 micrometers. In some cases, a thickness 302 can be a minimum thickness 302a, a maximum thickness 302b, or an average thickness (e.g., at a particular location of a gap 301 or evaluated over all or a portion of a length of gap 301, for example, where the length is perpendicular to the thickness and width of gap 301). In some cases, a gap 301 of an ultrasound device or system can have a width 303 of 1 micrometer to 25 micrometers, 1 micrometer to 50 micrometers, 1 micrometer to 100 micrometers, 1 micrometer to 150 micrometers, 1 micrometer to 200 micrometers, 1 micrometer to 250 micrometers, 1 micrometer to 500 micrometers, 1 micrometer to 750 micrometers, 1 micrometer to 1,000 micrometers, 25 micrometers to 50 micrometers, 25 micrometers to 100 micrometers, 25 micrometers to 150 micrometers, 25 micrometers to 200 micrometers, 25 micrometers to 250 micrometers, 25 micrometers to 500 micrometers, 25 micrometers to 750 micrometers, 25 micrometers to 1,000 micrometers, 50 micrometers to 100 micrometers, 50 micrometers to 150 micrometers, 50 micrometers to 200 micrometers, 50 micrometers to 250 micrometers, 50 micrometers to 500 micrometers, 50 micrometers to 750 micrometers, 50 micrometers to 1,000 micrometers, 100 micrometers to 150 micrometers, 100 micrometers to 200 micrometers, 100 micrometers to 250 micrometers, 100 micrometers to 500 micrometers, 100 micrometers to 750 micrometers, 100 micrometers to 1,000 micrometers, 150 micrometers to 200 micrometers, 150 micrometers to 250 micrometers, 150 micrometers to 500 micrometers, 150 micrometers to 750 micrometers, 150 micrometers to 1,000 micrometers, 200 micrometers to 250 micrometers, 200 micrometers to 500 micrometers, 200 micrometers to 750 micrometers, 200 micrometers to 1,000 micrometers, 250 micrometers to 500 micrometers, 250 micrometers to 750 micrometers, 250 micrometers to 1,000 micrometers, 500 micrometers to 750 micrometers, 500 micrometers to 1,000 micrometers, or 750 micrometers to 1,000 micrometers. In some cases, a gap 301 of an ultrasound device or system can have a width 303 of 1 micrometer, 25 micrometers, 50 micrometers, 100 micrometers, 150 micrometers, 200 micrometers, 250 micrometers, 500 micrometers, 750 micrometers, or 1,000 micrometers. In some cases, a gap 301 of an ultrasound device or system can have a width 303 of at least 1 micrometer, 25 micrometers, 50 micrometers, 100 micrometers, 150 micrometers, 200 micrometers, 250 micrometers, 500 micrometers, 750 micrometers, or 1,000 micrometers. In some cases, a gap 301 of an ultrasound device or system can have a width 303 of at most 1 micrometer, 25 micrometers, 50 micrometers, 100 micrometers, 150 micrometers, 200 micrometers, 250 micrometers, 500 micrometers, 750 micrometers, or 1,000 micrometers. In some cases, a gap 301 of an ultrasound device or system can have a width 303 (e.g., in a x-direction or a y-direction, as shown in FIG. 4, FIG. 5, FIG. 6, FIG. 7) of 1 micrometer (μm) to 2,000 micrometers. In some cases, a gap 301 of an ultrasound device or system can have a width 303 of 1 micrometer to 1,250 micrometers, 1 micrometer to 1,500 micrometers, 1 micrometer to 1,700 micrometers, 1 micrometer to 2,000 micrometers, 1,000 micrometer to 1,250 micrometers, 1,000 micrometer to 1,500 micrometers, 1,000 micrometer to 1,750 micrometers, 1,000 micrometer to 2,000 micrometers, 1,250 micrometers to 1,500 micrometers, 1,250 micrometers to 1,750 micrometers, 1,250 micrometers to 2,000 micrometers, 1,500 micrometers to 1,750 micrometers, 1,500 micrometers to 2,000 micrometers, or 1,750 micrometers to 2,000 micrometers. In some cases, a gap 301 of an ultrasound device or system can have a width 303 of 1,250 micrometers, 1,500 micrometers, 1,750 micrometers, or 2,000 micrometers. In some cases, a gap 301 of an ultrasound device or system can have a width 303 of at least 1,250 micrometers, 1,500 micrometers, 1,750 micrometers, or 2,000 micrometers. In some cases, a gap 301 of an ultrasound device or system can have a width 303 of at most 1 micrometer, 1,250 micrometers, 1,500 micrometers, 1,750 micrometers, or 2,000 micrometers.

In many cases, an outer barrier (e.g., a continuous outer barrier surrounding one or more internal components of an ultrasound system 100 or device 200) can resist or prevent intrusion of a liquid (e.g., water and/or a liquid disinfectant) into the interior of an ultrasound system 100 or device 200. In some cases, an interface 251 between a multilayer seal 240 and a lens 222 can prevent liquids from passing between the multilayer seal 240 and the lens 222 (e.g., a watertight interface). In some cases, an interface 252 between a multilayer seal 240 and a housing 231 can prevent liquids from passing between the multilayer seal 240 and the housing 231 (e.g., a watertight interface). In some cases, an outer surface (e.g., a distal surface) of an outer barrier at an interface 251 between a multilayer seal 240 and a lens 222 can be smooth (e.g., wherein a tangent of a distal surface of the multilayer seal 240 at the interface 251 has an angle equal to or substantially equal to (e.g., less than 5 degrees different than) the angle of a tangent of a distal surface of the lens 222 at the interface 251), for example, as shown in FIG. 5 and FIG. 6. In some cases, an outer surface (e.g., a distal surface) of an outer barrier at an interface 252 between a multilayer seal 240 and a housing 231 can be smooth (e.g., wherein a tangent of a distal surface of the multilayer seal 240 at the interface 252 has an angle equal to or substantially equal to (e.g., less than 5 degrees different than) the angle of a tangent of a distal surface of the housing 231 at the interface 252), for example, as shown in FIG. 5 and FIG. 6. Matching an angle of a tangents of a distal surface of the multilayer seal 240 and those of the housing 231 and/or the lens 222 (e.g., to create a smooth distal surface of the outer barrier) can aid in reducing the likelihood of water intrusion (e.g., reducing the likelihood of adhesive failure at an interface 251, 252 which could lead to water intrusion), can render low-level disinfection (e.g., comprising use of disinfectant wipes) easier to perform correctly, and can render the ultrasound device more comfortable to a patient's skin during use. In some cases, a distal surface of an outer barrier (or portion thereof) can be curved, for example, as shown in FIG. 5. In some cases, a distal surface of an outer barrier (or portion thereof) can be flat, for example, as shown in FIG. 6.

Figure 8:
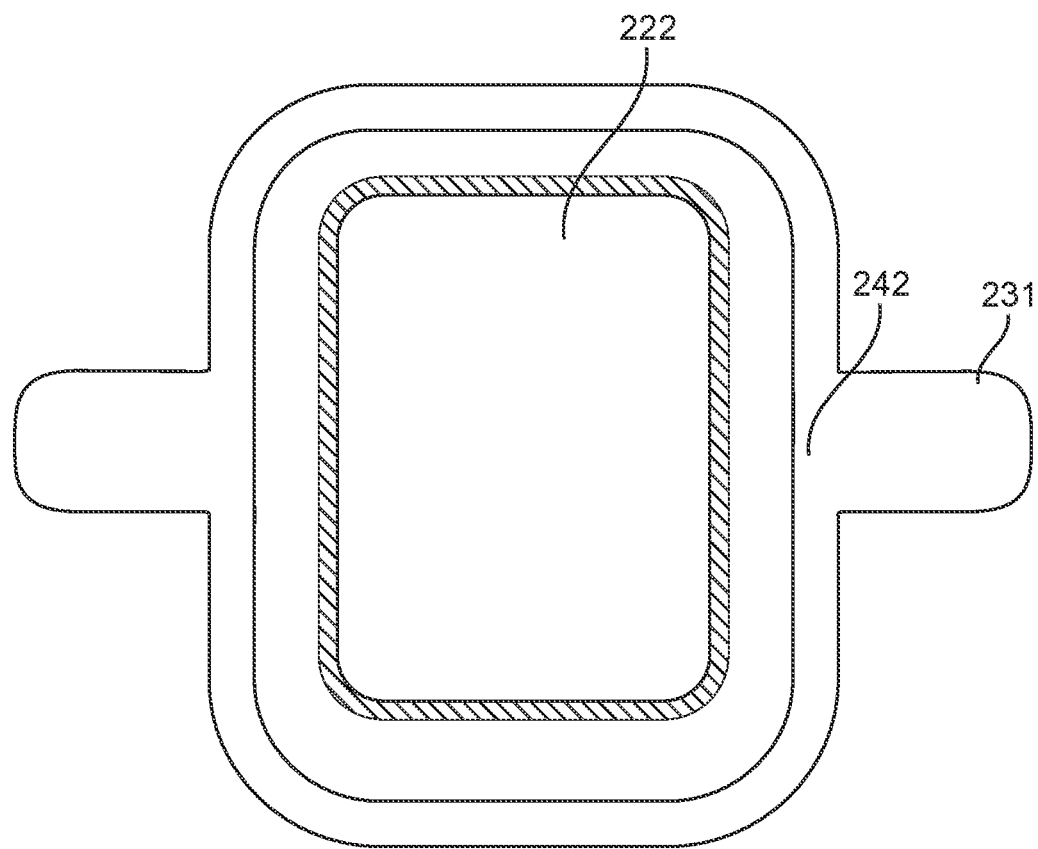
FIG. 8 shows an image of an indicator material showing a color change after exposure to a high-level disinfectant for 24 hours, in accordance with embodiments.

In some cases, a multilayer seal 240 can allow for detection of liquid intrusion into or through the outer barrier. In some cases, detection of liquid intrusion into an ultrasound device (e.g., an ultrasound probe head) can allow for identification of ultrasound devices that may require maintenance (e.g., resulting from liquid intrusion) or replacement (e.g., resulting from damage to one or more internal components due to liquid intrusion) of all or a portion of the device (e.g., all or a portion of the outer barrier of the device). In some cases, detection of liquid intrusion can prevent inadvertent use of an ultrasound system or device that is no longer calibrated and/or that is no longer capable of functioning accurately (e.g., as a result of liquid intrusion). In some cases, a first layer 242 of a multilayer seal 240 can be useful in detection of liquid intrusion. For example, a first layer 242 of a multilayer seal 240 can comprise an indicator material (e.g., an indicator film). In some cases, an indicator material (e.g., an indicator film) of a first layer 242 of a multilayer seal 240 can undergo a color change when contacted with a liquid (e.g., wherein the liquid comprises a disinfectant or wherein the liquid comprises water). For example, an indicator material of a first layer 242 can undergo a color change when contacted with a disinfectant (e.g., a low-level disinfectant or a high-level disinfectant). In some cases, an indicator material of a first layer 242 can undergo a color change when contacted with a first liquid and not when contacted with a second liquid. In some cases, an indicator material of the first layer 242 can undergo a color change when contacted with water. For example, an indicator material of a first layer 242 can undergo a color change when contacted with a first disinfectant (e.g., a high-level disinfectant) and not when contacted with a second disinfectant (e.g., a low-level disinfectant), in some cases. In some cases, an indicator material of a first layer 242 can undergo a color change when contacted with a low-level disinfectant and not when contacted with a high-level disinfectant. In some cases, an indicator material of a first layer 242 can undergo a color change when contacted with a first liquid (e.g., a high-level disinfectant or a low-level disinfectant) and not when contacted with a second liquid (e.g., water). For example, an indicator material of a first layer 242 can undergo a color change when contacted with a first liquid (e.g., water) and not when contacted with a second liquid (e.g., a high-level disinfectant or a low-level disinfectant). In some cases, an indicator material of the first layer 242 can change from a first color to a second color when contacted with a liquid (e.g., a specific liquid, such as water or a specific disinfectant, or when contacted with any liquid). In some cases, an indicator material of the first layer 242 can change from a first shade of a first color to a second shade of the first color when contacted with a liquid (e.g., a specific liquid, such as water or a specific disinfectant, or when contacted with any liquid). In some cases, a color change of a first layer (e.g., an indicator film or strip) can result from wetting of the first layer by a liquid (e.g., a liquid placed in contact with an outer surface of an ultrasound system or device during or between uses). In some cases, a color change of a first layer (e.g., an indicator film or strip) can result from a chemical reaction between a material of the first layer and a liquid or component thereof (e.g., a liquid or component thereof that is placed in contact with an outer surface of an ultrasound system or device during or between uses). In some cases, a first color can be white, yellow, or brown. In some cases, a second color can be yellow, brown, or black. For example, an indicator material can change from a first color of white to a second color of yellow, in some cases (e.g., when the indicator material is contacted with or incubated in contact with a liquid, such as a disinfectant). In some cases, a first color can be clear (e.g., colorless). In some cases, a second color can be clear (e.g., colorless). In some cases, a first layer 242 and/or an indicator material (e.g., comprising an indicator film or indicator strip) of a first layer 242 can comprise silicone or a silicone-based substance. In some cases, a first layer 242 and/or an indicator material of a first layer 242 can comprise one or more silicone-based substances selected from: ASI 505 (American Sealants, Inc.), ASI 306 (American Sealants, Inc.), ASI 388 (American Sealants, Inc.), Dow 734 (Dow Corning DOWSIL™ 734 Flowable Sealant), SS-154 (Silicone Solutions, Inc.), SS-265 (Silicone Solutions, Inc.), SS-6604 (Silicone Solutions, Inc.), or SS-18 (Silicone Solutions, Inc.). For example, a first layer can comprise a silicone-based substance (e.g., wherein the silicone-based substance comprises an indicator material (e.g., indicator film or indicator strip) of the first layer 242) comprising SS-18 (e.g., wherein the second color is yellow, for example, after the silicone-based substance is contacted with a high-level disinfectant, such as a disinfectant comprising benzene-1,2-dicarbaldehyde (e.g., phthalaldehyde, which can be ortho-phthalaldehyde (OPA)), for example, as shown in FIG. 8). In some cases, a first layer 242 can comprise a silicone-based substance (e.g., wherein the silicone-based substance comprises an indicator material (e.g., indicator film or indicator strip) of the first layer 242) comprising SS-6604 (e.g., wherein the second color is yellow, for example, after the silicone-based substance is contacted with a high-level disinfectant, such as a disinfectant comprising benzene-1,2-dicarbaldehyde (e.g., OPA)). In some cases, a first layer 242 can comprise a silicone-based substance (e.g., wherein the silicone-based substance comprises an indicator material (e.g., indicator film or indicator strip) of the first layer 242) comprising SS-265 (e.g., wherein the second color is brown, for example, after the silicone-based substance is contacted with a high-level disinfectant, such as a disinfectant comprising benzene-1,2-dicarbaldehyde (e.g., OPA)). In some cases, a first layer 242 can comprise a silicone-based substance (e.g., wherein the silicone-based substance comprises an indicator material (e.g., indicator film or indicator strip) of the first layer 242) comprising ASI 306 (e.g., wherein the second color is yellow, for example, after the silicone-based substance is contacted with a high-level disinfectant, such as a disinfectant comprising benzene-1,2-dicarbaldehyde (e.g., OPA)). In some cases, a first layer 242 can comprise a silicone-based substance (e.g., wherein the silicone-based substance comprises an indicator material (e.g., indicator film or indicator strip) of the first layer 242) comprising ASI 388 (e.g., wherein the second color is yellow, for example, after the silicone-based substance is contacted with a high-level disinfectant, such as a disinfectant comprising benzene-1,2-dicarbaldehyde (e.g., OPA)). In some cases, a silicone-based substance described herein (e.g., comprising a component of a first layer 242, a second layer 244, and/or a third layer 246) can comprise a "one-part" silicone substance (e.g., a one-part silicone-based adhesive or sealant), which may comprise a first part (e.g., a rubber base) and a second part (e.g., a curing agent). In some cases, a one-part silicone substance can be advantageous for use as component of a first layer 242 (or a second layer 244 or a third layer 246), for example, because one-part silicone substances (e.g., one-part silicone-based adhesives or sealants) can be translucent or transparent when cured and/or because they can cure quickly and/or without a need for mixing, in some cases. In some cases, a silicone-based substance described herein (e.g., comprising a component of a first layer 242, a second layer 244, and/or a third layer 246) can comprise a "two-part" silicone, which may comprise a first part (e.g., a silicone rubber base) and a second part (e.g., a curing agent). In some cases, a first layer 242 and/or an indicator material of a first layer 242 can comprise a self-leveling adhesive, e.g., a silicone-based self-leveling adhesive, such as SS-18. In some cases, a first layer 242 and/or an indicator material of a first layer 242 can comprise a thixotropic adhesive, e.g., a silicone-based thixotropic adhesive, such as SS-19. In some cases, a silicone-based substance (e.g., comprising a component of a first layer 242, a second layer 244, and/or a third layer 246) can utilize one or more of a moisture curing system, an ultraviolet UV curing system, a heat curing system, and/or a room-temperature-vulcanizing (RTV) silicone curing system. For example, a one-part silicone-based substance can use moisture in the air to cure, in some embodiments.

In some cases, a first layer 242 (e.g., wherein the first layer comprises an indicator material) can be in direct contact with an internal component of an ultrasound system or device. In some cases, a first layer 242 can be the most proximal layer of a multilayer seal 240. For example, a first layer 242 of a multilayer seal 240 can be in direct contact with a proximal surface of a second layer 244 of the multilayer seal 240 and a distal surface of an internal component of an ultrasound system or device, for example, as shown in FIG. 5 and FIG. 6. In some cases, a first layer 242 of a multilayer seal 240 can be in direct contact with a proximal surface of a second layer 244 of the multilayer seal 240 and not in direct contact with a third layer 246 of the multilayer seal 240 (e.g., as shown in FIG. 5 and FIG. 6). In some cases, a first layer 242 of a multilayer seal 240 can be in direct contact with both a second layer 244 (e.g., a distal surface of a second layer 244) and in direct contact with a third layer 246 (e.g., a proximal surface of a third layer 246) of the multilayer seal 240 (e.g., as shown in FIG. 7). In some cases, positioning the first layer 242 of a multilayer seal 240 between a second layer 244 and a third layer 246 of the multilayer seal 240 can provide an indication of liquid intrusion when a liquid has traversed some but not all layers of the multilayer seal 240 that are capable of preventing liquid flow across an outer barrier comprising the multilayer seal 240, which can facilitate repair of a partially compromised outer barrier before internal components are affected (e.g., damaged) by liquid intrusion.

A first layer 242 can be in contact with an internal component of an ultrasound system or device. For example, a first layer 242 can be in contact with a MEMS transducer array 202, a MEMS wafer, or an ASIC 106, or a heat management component 268 of the ultrasound system or device. In some cases, a first layer 242 can be placed in contact with (e.g., adhered to) an internal component of an ultrasound system or device before a second layer 244 (or a third layer 246) of a multilayer seal 240 are placed in contact with the first layer 242. In some cases, a first layer 242 can comprise an adhesive. In some cases, a first layer 242 is applied to an internal component of the ultrasound system or device such that no wrinkles or gaps are present between the first layer and the internal component and/or the housing and/or the lens. In some cases, a multilayer seal can still effectively reduce the likelihood of liquid intrusion into the interior of an ultrasound system or device (and/or provide an indication of liquid intrusion) even when one or more wrinkles or gaps (e.g., from wrinkling, perforation, or tearing of the first layer 242) are present between the first layer 242 and the internal component and/or the housing and/or the lens, for instance, because the second layer 244 (and, in some cases, the third layer 246) can provide liquid barrier function for the multilayer seal 240. This can be an advantage over other approaches, such as the use of rubber or plastic gaskets in place of a multilayer seal 240. In some cases, a second layer 244, which can be a thixotropic material, can be in contact with the entire (e.g., distal) surface of a first layer 242, for example, even when the first layer 242 is wrinkled, perforated, or torn.

In some cases, a first layer 242 (e.g., comprising an indicator material) can have a thickness (e.g., in the z-direction, as shown in FIG. 5 and FIG. 6) of 1 micrometer (μm) to 150 micrometers. In some cases, a first layer (e.g., comprising an indicator material) can have a thickness of 1 micrometer to 25 micrometers, 1 micrometer to 50 micrometers, 1 micrometer to 75 micrometers, 1 micrometer to 100 micrometers, 1 micrometer to 125 micrometers, 1 micrometer to 150 micrometers, 25 micrometers to 50 micrometers, 25 micrometers to 75 micrometers, 25 micrometers to 100 micrometers, 25 micrometers to 125 micrometers, 25 micrometers to 150 micrometers, 50 micrometers to 75 micrometers, 50 micrometers to 100 micrometers, 50 micrometers to 125 micrometers, 50 micrometers to 150 micrometers, 75 micrometers to 100 micrometers, 75 micrometers to 125 micrometers, 75 micrometers to 150 micrometers, 100 micrometers to 125 micrometers, 100 micrometers to 150 micrometers, or 125 micrometers to 150 micrometers. In some cases, a first layer (e.g., comprising an indicator material) can have a thickness of 1 micrometer, 25 micrometers, 50 micrometers, 75 micrometers, 100 micrometers, 125 micrometers, or 150 micrometers. In some cases, a first layer (e.g., comprising an indicator material) can have a thickness of at least 1 micrometer, 25 micrometers, 50 micrometers, 75 micrometers, 100 micrometers, 125 micrometers, or 150 micrometers. In some cases, a first layer (e.g., comprising an indicator material) can have a thickness of at most 1 micrometer, 25 micrometers, 50 micrometers, 75 micrometers, 100 micrometers, 125 micrometers, or 150 micrometers. In some cases, a first layer (e.g., comprising an indicator material) can have a width (e.g., in a x-direction and/or a y-direction, as shown in FIG. 4) of 10 percent to 100 percent of a width 303 of a gap 301. In some cases, a first layer (e.g., comprising an indicator material) can have a width of 10 percent to 25 percent, 10 percent to 50 percent, 10 percent to 75 percent, 10 percent to 100 percent, 25 percent to 50 percent, 25 percent to 75 percent, 25 percent to 100 percent, 50 percent to 75 percent, 50 percent to 100 percent, or 75 percent to 100 percent of a width of a gap 301. In some cases, a first layer (e.g., comprising an indicator material) can have a width of 10 percent, 25 percent, 50 percent, 75 percent, or 100 percent of a gap 301. In some cases, a first layer (e.g., comprising an indicator material) can have a width of at least 10 percent, 25 percent, 50 percent, 75 percent, or 100 percent of a width of a gap 301. In some cases, a first layer (e.g., comprising an indicator material) can have a width of at most 10 percent, 25 percent, 50 percent, 75 percent, or 100 percent of a width of a gap 301. In some cases, a first layer (e.g., comprising an indicator material) can have a thickness of 5 percent to 100 percent of a thickness 302 of a gap 301. In some cases, a first layer (e.g., comprising an indicator material) can have a thickness of 5 percent to 12 percent, 5 percent to 25 percent, 5 percent to 37 percent, 5 percent to 50 percent, 5 percent to 75 percent, 5 percent to 100 percent, 12 percent to 25 percent, 12 percent to 37 percent, 12 percent to 50 percent, 12 percent to 75 percent, 12 percent to 100 percent, 25 percent to 37 percent, 25 percent to 50 percent, 25 percent to 75 percent, 25 percent to 100 percent, 37 percent to 50 percent, 37 percent to 75 percent, 37 percent to 100 percent, 50 percent to 75 percent, 50 percent to 100 percent, or 75 percent to 100 percent of a thickness 302 of a gap 301. In some cases, a first layer (e.g., comprising an indicator material) can have a thickness of 5 percent, 12 percent, 25 percent, 37 percent, 50 percent, 75 percent, or 100 percent of a thickness 302 of a gap 301. In some cases, a first layer (e.g., comprising an indicator material) can have a thickness of at least 5 percent, 12 percent, 25 percent, 37 percent, 50 percent, 75 percent, or 100 percent of a thickness 302 of a gap 301. In some cases, a first layer (e.g., comprising an indicator material) can have a thickness of at most 5 percent, 12 percent, 25 percent, 37 percent, 50 percent, 75 percent, or 100 percent of a thickness 302 of a gap 301.

A multilayer seal 240 can comprise a second layer 244. In some cases, the second layer 244 can function as a barrier to liquid intrusion into an interior compartment or space of an ultrasound system or device. In some cases, a second layer 244 can be disposed in a gap 301 between a lens 222 and a housing 231 (e.g., at a distal end of an ultrasound device). In some cases, a second layer 244 of a multilayer seal 240 can be adhesive. For example, a second layer 244 of a multilayer seal 240 can be adherent to (e.g., strongly adherent to) a side wall of a housing 231 (e.g., a side wall of an aperture of a housing 231) of an ultrasound device. In some cases, a second layer 244 of a multilayer seal 240 can be adherent to (e.g., strongly adherent to) a side wall of a lens 222 of an ultrasound device. In some cases, a second layer 244 of a multilayer seal 240 can be adherent to (e.g., strongly adherent to) a surface of an internal component of an ultrasound device. In some cases, a second layer 244 can comprise a material that can flow under pressure (e.g., a material having a high-viscosity, such as a thixotropic material). In some cases, a second layer 244 comprises a material that is highly viscous. In some cases, a second layer 244 comprises a material that will deform under pressure but will not flow in the absence of applied pressure. In some cases, a material that will deform under pressure allows the material to be deposited over a desired area. In some cases, a material that will deform under pressure allows the material to fill gaps, crevices, wrinkles, or undulations in a surface to which it is applied. In some cases, a material that will not flow in the absence of applied pressure is useful as a second layer material, e.g., because the material will not flow into the interior of the ultrasound device after it is deposited in a gap 301. In some cases, a second layer 244 can comprise silicone or a silicone-based substance. For instance, a material of a second layer 244 can comprise silicone. In some cases, a second layer can comprise a sealant (e.g., a silicone-based sealant) or an adhesive (e.g., a silicone-based adhesive). In some cases, a second layer 244 can comprise a thixotropic silicone-based substance (e.g., to allow flow under pressure but limit flow of the substance when pressure is removed, for example, to allow complete filling of wrinkles, holes, undulations, and/or gaps into which the substance is deposited or applied while, optionally, reducing spontaneous flow from a location of application or deposition). In some cases, a second layer 244 can comprise a self-leveling silicone-based substance. In some cases, a second layer 244 (e.g., a silicone-based sealant or silicone-based adhesive of a second layer) can comprise one or more silicone-based substances selected from: ASI 505 (American Sealants, Inc.), ASI 306 (American Sealants, Inc.), ASI 388 (American Sealants, Inc.), Dow 734 (Dow Corning DOWSIL™ 734 Flowable Sealant), SS-154 (Silicone Solutions, Inc.), SS-265 (Silicone Solutions, Inc.), SS-6604 (Silicone Solutions, Inc.), or SS-18 (Silicone Solutions, Inc.). In some cases, a second layer 244 can comprise a one-part silicone substance. In some cases, a material of a second layer 244 can be translucent. In some case, a material of a second layer 244 can be transparent (e.g., clear).

In some cases, a second layer 244 (e.g., a proximal surface of a second layer 244) can be in contact with all or a portion of a surface of a first layer 242 (e.g., a distal surface of a first layer 242), for example, as shown in FIG. 5 and FIG. 6. In some cases, a second layer 244 (e.g., a proximal surface of a second layer 244) can be in contact with all or a portion of a surface (e.g., a distal surface) of an internal component of an ultrasound device (e.g., an ultrasound transducer, a MEMS wafer, a MEMS array, or an ASIC), for example, as shown in FIG. 7. In some cases, a distal surface of a second layer 244 can be in contact with all or a portion of a surface of a first layer (e.g., as shown in FIG. 7). In some cases, a distal surface of a second layer 244 can be in contact with all or a portion of a surface of a third layer (e.g., as shown in FIG. 5 and FIG. 6).

In some cases, a second layer 244 of a multilayer seal 240 can have a thickness (e.g., in a z-direction, as shown in FIG. 5 and FIG. 6) of 1 micrometer (μm) to 1,000 micrometers. In some cases, a second layer 244 can have a thickness of 1 micrometer to 25 micrometers, 1 micrometer to 50 micrometers, 1 micrometer to 100 micrometers, 1 micrometer to 150 micrometers, 1 micrometer to 200 micrometers, 1 micrometer to 250 micrometers, 1 micrometer to 500 micrometers, 1 micrometer to 750 micrometers, 1 micrometer to 1,000 micrometers, 25 micrometers to 50 micrometers, 25 micrometers to 100 micrometers, 25 micrometers to 150 micrometers, 25 micrometers to 200 micrometers, 25 micrometers to 250 micrometers, 25 micrometers to 500 micrometers, 25 micrometers to 750 micrometers, 25 micrometers to 1,000 micrometers, 50 micrometers to 100 micrometers, 50 micrometers to 150 micrometers, 50 micrometers to 200 micrometers, 50 micrometers to 250 micrometers, 50 micrometers to 500 micrometers, 50 micrometers to 750 micrometers, 50 micrometers to 1,000 micrometers, 100 micrometers to 150 micrometers, 100 micrometers to 200 micrometers, 100 micrometers to 250 micrometers, 100 micrometers to 500 micrometers, 100 micrometers to 750 micrometers, 100 micrometers to 1,000 micrometers, 150 micrometers to 200 micrometers, 150 micrometers to 250 micrometers, 150 micrometers to 500 micrometers, 150 micrometers to 750 micrometers, 150 micrometers to 1,000 micrometers, 200 micrometers to 250 micrometers, 200 micrometers to 500 micrometers, 200 micrometers to 750 micrometers, 200 micrometers to 1,000 micrometers, 250 micrometers to 500 micrometers, 250 micrometers to 750 micrometers, 250 micrometers to 1,000 micrometers, 500 micrometers to 750 micrometers, 500 micrometers to 1,000 micrometers, or 750 micrometers to 1,000 micrometers. In some cases, a second layer 244 can have a thickness of 1 micrometer, 25 micrometers, 50 micrometers, 100 micrometers, 150 micrometers, 200 micrometers, 250 micrometers, 500 micrometers, 750 micrometers, or 1,000 micrometers. In some cases, a second layer 244 can have a thickness of at least 1 micrometer, 25 micrometers, 50 micrometers, 100 micrometers, 150 micrometers, 200 micrometers, 250 micrometers, 500 micrometers, 750 micrometers, or 1,000 micrometers. In some cases, a second layer 244 can have a thickness of at most 1 micrometer, 25 micrometers, 50 micrometers, 100 micrometers, 150 micrometers, 200 micrometers, 250 micrometers, 500 micrometers, 750 micrometers, or 1,000 micrometers. In some cases, a second layer 244 can have a thickness of 5 percent to 100 percent of a thickness 302 of a gap 301. In some cases, a second layer 244 can have a thickness of 5 percent to 10 percent, 5 percent to 25 percent, 5 percent to 50 percent, 5 percent to 63 percent, 5 percent to 75 percent, 5 percent to 87 percent, 5 percent to 100 percent, 10 percent to 25 percent, 10 percent to 50 percent, 10 percent to 63 percent, 10 percent to 75 percent, 10 percent to 87 percent, 10 percent to 100 percent, 25 percent to 50 percent, 25 percent to 63 percent, 25 percent to 75 percent, 25 percent to 87 percent, 25 percent to 100 percent, 50 percent to 63 percent, 50 percent to 75 percent, 50 percent to 87 percent, 50 percent to 100 percent, 63 percent to 75 percent, 63 percent to 87 percent, 63 percent to 100 percent, 75 percent to 87 percent, 75 percent to 100 percent, or 87 percent to 100 percent of a thickness 302 of a gap 301. In some cases, a second layer 244 can have a thickness of 5 percent, 10 percent, 25 percent, 50 percent, 63 percent, 75 percent, 87 percent, or 100 percent of a thickness 302 of a gap 301. In some cases, a second layer 244 can have a thickness of at least 5 percent, 10 percent, 25 percent, 50 percent, 63 percent, 75 percent, 87 percent, or 100 percent of a thickness of a gap 301. In some cases, a second layer 244 can have a thickness of at most 5 percent, 10 percent, 25 percent, 50 percent, 63 percent, 75 percent, 87 percent, or 100 percent of a thickness of a gap 301. In some cases, a second layer 244 can have a width (e.g., in a x-direction and/or a y-direction, as shown in FIG. 4) of at most 100 percent, at least 100 percent, or exactly 100 percent of a width 303 of a gap 301.

A multilayer seal 240 can comprise a third layer 246. In some cases, a third layer 246 can function as a barrier to liquid intrusion into an interior compartment or space of an ultrasound system or device. In some cases, a third layer 246 can be disposed in a gap 301 between a lens 222 and a housing 231 (e.g., at a distal end of an ultrasound device). In some cases, a third layer 246 of a multilayer seal 240 can be adhesive. For example, a third layer 246 of a multilayer seal 240 can be adherent to (e.g., strongly adherent to) a side wall of a housing 231 (e.g., a side wall of an aperture of a housing 231) of an ultrasound device. In some cases, a third layer 246 of a multilayer seal 240 can be adherent to (e.g., strongly adherent to) a side wall of a lens 222 of an ultrasound device. In some cases, a third layer 246 can comprise a material (e.g., a silicone-based substance) that is self-leveling (e.g., a self-leveling silicone adhesive or sealant). In some cases, a third layer 246 can comprise a material that can flow under pressure (e.g., a material having a high-viscosity, such as a thixotropic material). In some cases, a third layer 246 comprises a material that is highly viscous. In some cases, a third layer 246 comprises a material that can deform under pressure but will not flow in the absence of applied pressure. In some cases, a material that can deform under pressure allows the material to be deposited over a desired area. In some cases, a material that will deform under pressure allows the material to fill gaps, crevices, wrinkles, or undulations in a surface to which it is applied. In some cases, a third layer 246 can comprise silicone or a silicone-based substance. For instance, a material of a third layer 246 can comprise silicone. In some cases, a third layer 246 can comprise a sealant (e.g., a silicone-based sealant) or an adhesive (e.g., a silicone-based adhesive). In some cases, a third layer 246 can comprise a thixotropic silicone-based substance (e.g., to allow flow under pressure but limit flow of the substance when pressure is removed, for example, to allow complete filling of wrinkles, holes, undulations, and/or gaps into which the substance is deposited or applied while, optionally, reducing spontaneous flow from a location of application or deposition). In some cases, a third layer 246 can comprise a self-leveling silicone-based substance. In some cases, a third layer 246 (e.g., a silicone-based sealant or silicone-based adhesive of a third layer 246) can comprise one or more silicone-based substances selected from: ASI 505 (American Sealants, Inc.), ASI 306 (American Sealants, Inc.), ASI 388 (American Sealants, Inc.), Dow 734 (Dow Corning DOWSIL™ 734 Flowable Sealant), SS-154 (Silicone Solutions, Inc.), SS-265 (Silicone Solutions, Inc.), SS-6604 (Silicone Solutions, Inc.), or SS-18 (Silicone Solutions, Inc.). In some cases, a third layer 246 can comprise a one-part silicone substance. In some cases, a third layer 246 comprises one or more of the same materials as the third layer 246. In some cases, a third layer 246 comprises a different ratio of the same materials as the second layer 244 (e.g., to bestow a lower viscosity on the material of the third layer 246). In some cases, a third layer 246 can comprise a material that has a lower viscosity than that of a second layer 244 of the multilayer seal 240. For example, a third layer 246 of a multilayer seal 240 can comprise a self-leveling silicone-based substance and a second layer 246 of a multilayer seal 240 can comprise a thixotropic silicone-based substance. In some cases, a lower viscosity in a third layer material 246 (e.g., relative to that of a second layer material) can aid in establishing a smooth distal (e.g., external) surface of the third layer, even in situations when the third layer is added to an uneven surface (e.g., as shown in FIG. 5), for example, because the third layer material (which may comprise a self-leveling silicone-based substance) may have a lower viscosity than the surface to which it is applied or on which it is deposited. In some cases, a material of a third layer 246 can be translucent. In some case, a material of a third layer 246 can be transparent (e.g., clear). In some cases, a third layer 246 that is translucent or transparent can allow for observation of a color change (or absence thereof) in a material of a first layer 242 from through the third layer 246 material. In some cases, a material for a third layer 246 can be selected for its chemical interactions with a side wall of a lens or a side wall of a housing. For instance, a material for a third layer 246 can be selected such that it will settle (e.g., flow slightly) such that a wetting angle of the material decreases over time to become closer to (or equal to) an angle of a side wall (e.g., a housing side wall or a lens side wall), for example, without changing the height of the highest contact point between the material and the side wall. In some cases, a material of a multilayer seal 240 (e.g., a material of a third layer 246 or, in some cases, a material of a second layer 244) can be polished, burnished, cut, or otherwise smoothed to match an angle of one or more of a distal surface of a housing 231 at an interface 252 of the material and the housing or of a lens 222 at an interface 251 of the material and the lens. In some cases, a risk of delamination (e.g., during disinfection cleaning) of an outer barrier (e.g., an external surface, which can include a distal surface) of an ultrasound device or system can be decreased when a distal layer (e.g., a third layer 246, which may be a self-leveling layer, or, in some cases, a second layer 244, which may be a thixotropic layer) of a multilayer seal has an angle (e.g., as measured by a tangent) at an interface 251, 252 that matches or approximately matches an angle of a distal surface of a lens 222 or a housing 231 at the interface 251, 252.

In some cases, a third layer 246 (e.g., a proximal surface of a third layer 246) can be in contact with all or a portion of a surface of a first layer 242 (e.g., a distal surface of a first layer 242), for example, as shown in FIG. 7. In some cases, a third layer 246 (e.g., a proximal surface of a third layer 246) can be in contact with all or a portion of a surface of a second layer 244 (e.g., a distal surface of a second layer 244), for example, as shown in FIG. 5 and FIG. 6. In some cases, a distal surface of a third layer 246 can comprise a portion of a distal surface of an outer barrier (e.g., as shown in FIG. 5, FIG. 6, and FIG. 7).

In some cases, a third layer 246 of a multilayer seal 240 can have a thickness (e.g., in a z-direction, as shown in FIG. 5 and FIG. 6) of 1 micrometer (μm) to 1,000 micrometers. In some cases, a third layer 246 can have a thickness of 1 micrometer to 25 micrometers, 1 micrometer to 50 micrometers, 1 micrometer to 100 micrometers, 1 micrometer to 150 micrometers, 1 micrometer to 200 micrometers, 1 micrometer to 250 micrometers, 1 micrometer to 500 micrometers, 1 micrometer to 750 micrometers, 1 micrometer to 1,000 micrometers, 25 micrometers to 50 micrometers, 25 micrometers to 100 micrometers, 25 micrometers to 150 micrometers, 25 micrometers to 200 micrometers, 25 micrometers to 250 micrometers, 25 micrometers to 500 micrometers, 25 micrometers to 750 micrometers, 25 micrometers to 1,000 micrometers, 50 micrometers to 100 micrometers, 50 micrometers to 150 micrometers, 50 micrometers to 200 micrometers, 50 micrometers to 250 micrometers, 50 micrometers to 500 micrometers, 50 micrometers to 750 micrometers, 50 micrometers to 1,000 micrometers, 100 micrometers to 150 micrometers, 100 micrometers to 200 micrometers, 100 micrometers to 250 micrometers, 100 micrometers to 500 micrometers, 100 micrometers to 750 micrometers, 100 micrometers to 1,000 micrometers, 150 micrometers to 200 micrometers, 150 micrometers to 250 micrometers, 150 micrometers to 500 micrometers, 150 micrometers to 750 micrometers, 150 micrometers to 1,000 micrometers, 200 micrometers to 250 micrometers, 200 micrometers to 500 micrometers, 200 micrometers to 750 micrometers, 200 micrometers to 1,000 micrometers, 250 micrometers to 500 micrometers, 250 micrometers to 750 micrometers, 250 micrometers to 1,000 micrometers, 500 micrometers to 750 micrometers, 500 micrometers to 1,000 micrometers, or 750 micrometers to 1,000 micrometers. In some cases, a third layer 246 can have a thickness of 1 micrometer, 25 micrometers, 50 micrometers, 100 micrometers, 150 micrometers, 200 micrometers, 250 micrometers, 500 micrometers, 750 micrometers, or 1,000 micrometers. In some cases, a third layer 246 can have a thickness of at least 1 micrometer, 25 micrometers, 50 micrometers, 100 micrometers, 150 micrometers, 200 micrometers, 250 micrometers, 500 micrometers, 750 micrometers, or 1,000 micrometers. In some cases, a third layer 246 can have a thickness of at most 1 micrometer, 25 micrometers, 50 micrometers, 100 micrometers, 150 micrometers, 200 micrometers, 250 micrometers, 500 micrometers, 750 micrometers, or 1,000 micrometers. In some cases, a third layer 246 can have a thickness of 5 percent to 100 percent of a thickness 302 of a gap 301. In some cases, a third layer 246 can have a thickness of 5 percent to 10 percent, 5 percent to 25 percent, 5 percent to 50 percent, 5 percent to 63 percent, 5 percent to 75 percent, 5 percent to 87 percent, 5 percent to 100 percent, 10 percent to 25 percent, 10 percent to 50 percent, 10 percent to 63 percent, 10 percent to 75 percent, 10 percent to 87 percent, 10 percent to 100 percent, 25 percent to 50 percent, 25 percent to 63 percent, 25 percent to 75 percent, 25 percent to 87 percent, 25 percent to 100 percent, 50 percent to 63 percent, 50 percent to 75 percent, 50 percent to 87 percent, 50 percent to 100 percent, 63 percent to 75 percent, 63 percent to 87 percent, 63 percent to 100 percent, 75 percent to 87 percent, 75 percent to 100 percent, or 87 percent to 100 percent of a thickness 302 of a gap 301. In some cases, a third layer 246 can have a thickness of 5 percent, 10 percent, 25 percent, 50 percent, 63 percent, 75 percent, 87 percent, or 100 percent of a thickness 302 of a gap 301. In some cases, a third layer 246 can have a thickness of at least 5 percent, 10 percent, 25 percent, 50 percent, 63 percent, 75 percent, 87 percent, or 100 percent of a thickness of a gap 301. In some cases, a third layer 246 can have a thickness of at most 5 percent, 10 percent, 25 percent, 50 percent, 63 percent, 75 percent, 87 percent, or 100 percent of a thickness of a gap 301. In some cases, a third layer 246 can have a width (e.g., in a x-direction and/or a y-direction, as shown in FIG. 4) of at most 100 percent, at least 100 percent, or exactly 100 percent of a width 303 of a gap 301.

In some cases, an ultrasound system 100 or device 200 that does not comprise a multilayer seal can be less effective at preventing liquid intrusion into an interior of the ultrasound system 100 or device 200 than an ultrasound system 100 or device 200 that comprises a multilayer seal. For example, it may be challenging to seat a gasket (e.g., a rubber or polymer-based gasket) disposed between and in contact with a housing 231 and lens 222 (e.g., fully or partially filling gap 301) properly between the housing 231 and the lens 222 (and/or on a substrate of the interior of the device 200, such as a MEMS array or an ASIC wafer). In some cases, gaskets can be prefabricated and manipulated into position with other components of an outer barrier during assembly of an ultrasound device. In some cases, a prefabricated gasket can have a specific shape and/or specific dimensions. In some cases, a specific shape and/or specific set of dimensions of a prefabricated gasket may not match one or more shape and dimensions of a gap 301 of an ultrasound device 200. For example, a shape and/or dimension of a gap 301 may not match nominal values included in the device design (for example due to imprecision in lens and/or housing shapes and/or dimensions, temperature of component(s) during assembly, and/or the pressure used to assemble the device). In some cases, a gasket (e.g., a prefabricated gasket) cannot be modified easily to fit the actual dimensions of gap 301 (e.g., as opposed to the expected dimensions of gap 301 from device designs), which may lead to incomplete and/or ineffective contact between the gasket and the lens and/or between the gasket and the housing. In some cases, it may be difficult to apply a gasket to a surface of the device (e.g., during device assembly) such that the gasket lies flat (e.g., without wrinkles) on the surface to which it is applied. In some cases, manipulation of a gasket during assembly can result in perforation or tearing of the gasket, which can adversely affect the barrier function of the gasket. In some cases, incomplete or ineffective contact between the gasket and one or more other components of the outer barrier of an ultrasound device can negatively affect the barrier function of the outer barrier and can, in some cases, render the device susceptible to liquid intrusion. In some cases, compressing a gasket between the lens and/or the housing and/or between an internal component (e.g., an ASIC wafer or MEMS wafer) can improve the contact of the gasket with one or more of the lens and the housing; however, compression can be ineffective or even detrimental in some cases. For example, compression of a gasket (e.g., a prefabricated rubber or plastic gasket) may not provide sufficient deformation of the gasket to fully fill a width of gap 301 (e.g., from a side of lens 222 to a side of housing 231). Additionally, modulating the pressure with which the components of an ultrasound device are assembled (and/or compressed) could potentially adversely affect the alignment and/or flexure of one or more other components of the device (e.g., an ultrasound transducer). In contrast, a multilayer seal 240 can allow for high tolerances in ultrasound device component shapes and sizes without appreciably affecting the barrier function of the outer barrier. For example, a viscous second layer 244 of a multilayer seal 240 can be formed within gap 301 after assembly of the housing and lens 222 (and, optionally, one or more interior components of the device). In some cases, a second layer 244 (or third layer) capable of flowing (e.g., wherein the degree of flow is dictated at least in part by the viscosity of the layer material) can match variations (e.g., imperfections or undulations) in the shape or dimensions of the gap. In some cases, this can establish a water-resistant or watertight seal, even when the gap shape or dimensions are not consistent with expected shapes or dimensions.

A housing 231 can substantially surround (e.g., spatially encompass) one or more internal components (e.g., comprising an ultrasound transducer (e.g., comprising a MEMS array), an ASIC, and/or a computer processor or controller), of an ultrasound system or device. In some cases, a housing can comprise all or a portion of an outer barrier of an ultrasound system or device. For example, a housing 231 can comprise lateral sides 262 spatially encompassing one or more internal components of the ultrasound system or device around a longitudinal axis "z," for example as shown in FIG. 2. In some cases, a housing 231 can comprise one or more proximal sides 264 spatially encompassing all or a portion of one or more internal components of the ultrasound system or device at a proximal end of a longitudinal axis "z" of an ultrasound device, e.g., as shown in FIG. 2. In some cases, a housing 231 can comprise one or more distal sides 260 spatially encompassing all or a portion of one or more internal components of the ultrasound system or device at a distal end of a longitudinal axis "z" of an ultrasound device, for example, as shown in FIG. 2. In some cases, one or more internal components of an ultrasound system or device can be spatially encompassed (e.g., bounded) at a distal end of the ultrasound device by an outer barrier comprising a multilayer seal 240, a lens 222, and at least a portion of housing 231. As described herein, a lens can be coupled to a multilayer seal 240 (e.g., at an interface 252, which may comprise the entirety of a lateral perimeter surface of the housing 231 at a distal end, for instance a lateral surface of an aperture of the housing 231 at distal end of the ultrasound device), for instance to prevent liquid intrusion around the housing 231 and into the interior of the ultrasound system or device. A housing can be a single piece of material (e.g., a single segment). In some cases, a housing comprises multiple pieces of material (e.g., a plurality of segments) coupled together, for example, at one or more watertight or water resistant joints. In some cases, a housing 231 of an ultrasound system or device can comprise a plastic (e.g., a polycarbonate, a polyester, polyethylene terephthalate, polybutylene terephthalate, or a combination thereof), a resin, and/or a metal. In some cases, a housing 231 of an ultrasound system or device can be added to the ultrasound system or device after assembly of the lens and one or more internal component(s) (e.g., comprising an ultrasound transducer). In some cases, it can be more cost effective to fabricate a housing 231 to have a shape and/or dimensions such that a small gap 301 is left between the housing 231 and the lens 222, for instance, to allow greater tolerance in the fit of the housing with the assembled lens and ultrasound transducer. In some cases, it can be advantageous to incorporate a seal (e.g., a multilayer seal described herein) between the assembled housing 231 and lens 222, for instance to reduce water intrusion between the housing 231 and the lens 222.

A lens 222 (e.g., an acoustic lens 222) can comprise an acoustically and/or optically translucent or transparent material. In many cases, a lens 222 can function to transmit ultrasound energy waves to and/or from an ultrasound transducer of an ultrasound system or device. In many cases, a lens 222 can be located at a distal end of an ultrasound system or device. In some cases, all or a portion of a lens 222 can form a portion of an outer barrier of an ultrasound system or device. For example, a distal surface (e.g., an outer surface) of a lens 222 can function to prevent liquids from penetrating into an interior of an ultrasound device (e.g., an ultrasound probe head). In some cases, a lens 222 can comprise an outer coating (e.g., to improve acoustic impedance transition from the transducer to the acoustic gel or tissue of a patient and/or to reduce the lens' 222 susceptibility to scratches), which may form a part of the outer barrier. As described herein, a lens 222 can be coupled to a multilayer seal 240 (e.g., at an interface 251, which may comprise the entirety of a lateral perimeter surface of the lens 222), for instance to prevent liquid intrusion around the lens 222 and into the interior of the ultrasound system or device. In some cases, a lens 222 can be coupled to an ultrasound transducer (e.g., at a proximal surface of the lens 222). In some cases, a lens 222 can be (e.g., directly) coupled to a MEMS array, a MEMS wafer, or an ASIC wafer (e.g., at a proximal surface of the lens 222).

Multilayer Seals

A multilayer seal can comprise a plurality of layers. In some embodiments, a multilayer seal 240 can comprise two, three, four, five, six, seven, eight, nine, ten, ten to twenty, or more than twenty layers. In some cases, a multilayer seal 240 can comprise a plurality of first layers. For instance, a multilayer seal 240 can comprise two, three, four, five, or more than five first layers. In some cases, a first first layer can comprise a material that undergoes a color change when placed in contact with water. In some cases, a first first layer can comprise a material that undergoes a color change when placed in contact with a disinfectant. In some cases, a multilayer seal 240 can comprise a second first layer, for example, wherein the second first layer comprises a material that undergoes a color change when placed in contact with a different liquid than the liquid capable of causing a color change in a first first layer. For instance, a multilayer seal 240 can comprise a first first layer that can undergo a color change when placed in contact with water and a second first layer that can undergo a color change when placed in contact with a disinfectant (e.g., a high-level disinfectant). In some cases, a multilayer seal 240 can comprise a second first layer that comprises a material that undergoes a color change (e.g., a different color change) when placed in contact with the same liquid capable of causing a color change in the first first layer of the multilayer seal 240. In some cases, a second first layer can be in direct contact with a first first layer of a multilayer seal 240. In some cases, a second first layer may not be in direct contact with a first first layer of a multilayer seal 240. For instance, a second first layer may be disposed between (e.g., and in contact with) a second layer 244 of the multilayer seal 240 and a third layer 246 of the multilayer seal 240, while a first first layer of the multilayer seal 240 may be disposed proximal to the second layer 244 of the multilayer seal (e.g., to indicate an extent of liquid intrusion into the ultrasound device).

Figure 9A:
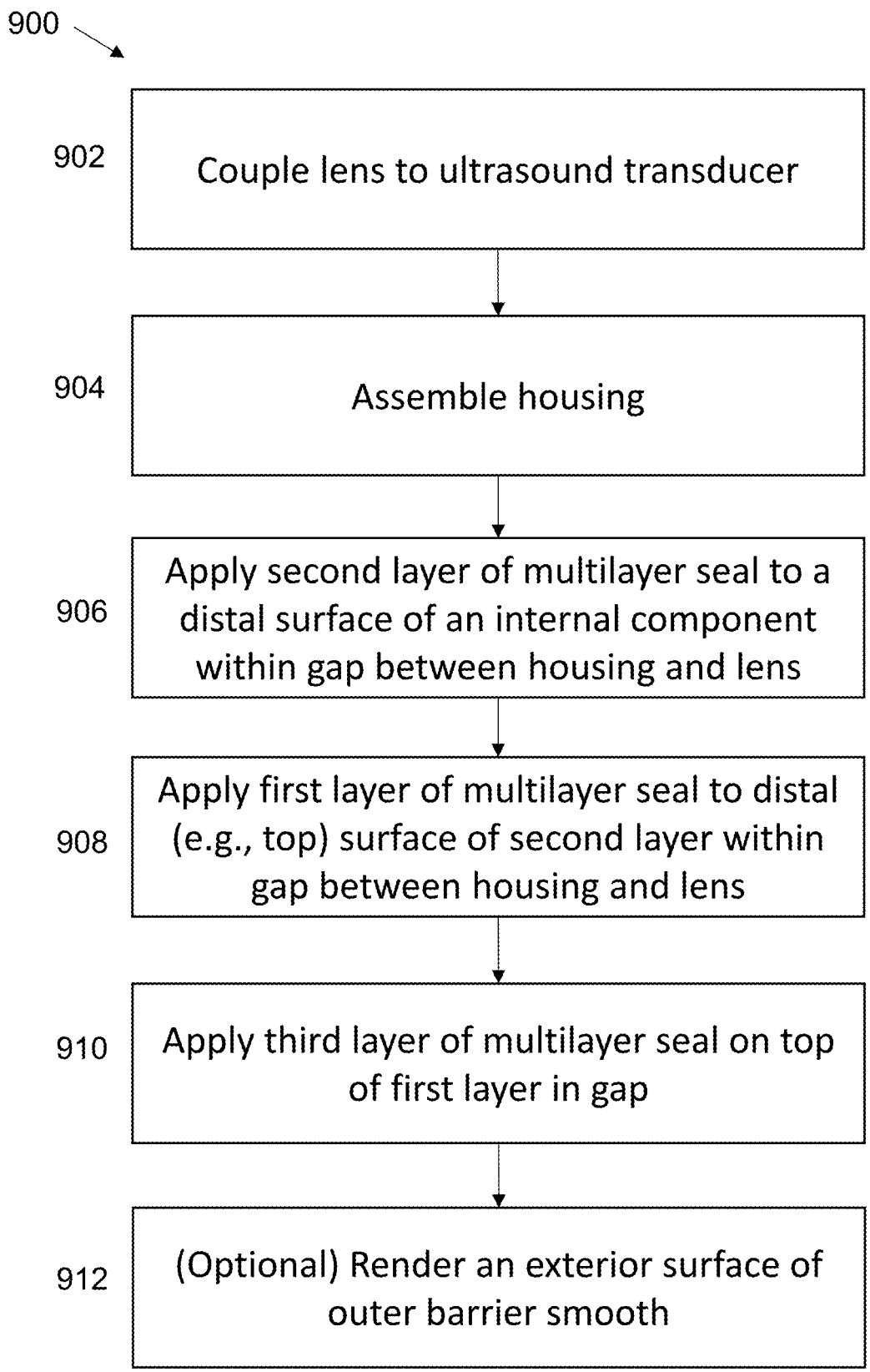
FIG. 9A shows steps of a method for fabrication of an outer barrier of an ultrasound device comprising a multilayer seal, in accordance with embodiments.

FIG. 9A shows an example of steps of a method 900 of fabricating an ultrasound system or device comprising a multilayer seal. In some cases, a lens 222 can be coupled to one or more internal components (e.g., such as an ultrasound transducer) of the ultrasound device (e.g., wherein the lens 222 is directly or indirectly coupled to the one or more internal components of the ultrasound device) (e.g., as shown in step 902). In some cases, a housing can be assembled (e.g., partially) around the coupled lens and internal component(s) (e.g., as shown in step 904). A second layer 244 of the multilayer seal 240 (e.g., an adhesive, thixotropic second layer) can be applied to an interior surface (e.g., a distal surface of an internal component) of a gap 301 between the housing 231 and the lens 222, for example, by using a needle (e.g., a dispensing needle) to dispense the second layer 244 onto the interior surface (e.g., wherein the second layer 244 is applied such that it is in contact with the entirety of a perimeter of a side wall of the housing 231, in contact with the entirety of a perimeter of a side wall of the lens 222, and in contact with the entire distal surface of the interior surface), for example, as shown in step 906. In some cases, a first layer 242 of the multilayer seal 240 can be applied to a distal surface of the second layer 244 of the multilayer seal 240 after the second layer 244 has been applied within the gap 301 (e.g., as shown in step 908). In some cases, a third layer 246 (e.g., an adhesive third layer, which may comprise the same material(s) as the second layer 244 in the same or different proportions as the second layer) can be applied to a distal surface of the first layer within the gap 301 (e.g., wherein the third layer 246 is applied such that it is in contact with the entirety of a perimeter of a side wall of the housing 231, in contact with the entirety of a perimeter of a side wall of the lens 222, and in contact with the entire distal surface of the first layer 242), for example, as shown in step 910 of FIG. 9A. In some cases, an exterior (e.g., distal) surface of a multilayer seal 240 (e.g., an exterior surface of a second layer 244 or a third layer 246 of the multilayer seal 240) can be smooth (e.g., coplanar or approximately coplanar) at a first interface 251 with respect to an exterior (e.g., distal) surface of the lens 222 and/or at a second interface 252 with respect to an exterior (e.g., distal) surface of the housing 231. In some cases, a first surface (e.g., an exterior surface of a multilayer seal 240) can be smooth with respect to a second surface (e.g., an exterior surface of a lens 222 or a housing 231) when an angle tangent to all or a portion of the first surface matches (e.g., is equal to or is supplementary to) or approximately matches (e.g., within 1%, within 5%, within 10%, within 15%, within 20%, within 25%, or within 30% of being equal to or supplementary to) an angle tangent to all or a portion of the second surface at an interface (e.g., interface 251 or interface 252) between the first surface and the second surface. In some cases, a first surface (e.g., an exterior surface of a multilayer seal 240) can be smooth with respect to a second surface (e.g., an exterior surface of a lens 222 or a housing 231) when there is no disjunction (e.g., gap) between the first and second surface or when there is no surface irregularity or roughness in the first and second surfaces at an interface (e.g., interface 251 or interface 252) of the first and second surfaces. In some cases, the exterior (e.g., distal) surface of the third layer 246 can be rendered smooth, e.g., by cutting, grinding, or polishing the distal surface of the third layer 246 until an angle of a tangent of the third layer 246 matches (or approximately matches, e.g., within 10% or within 25%) the angle of a tangent of the lens 222 at a first interface 251 and/or until an angle of a tangent of the distal surface of the third layer 246 matches (or approximately matches, e.g., within 10% or within 25%) the angle of a tangent of a distal surface of the housing 231 at a second interface 252 (e.g., as shown in step 912 of FIG. 9A).

Figure 9B:
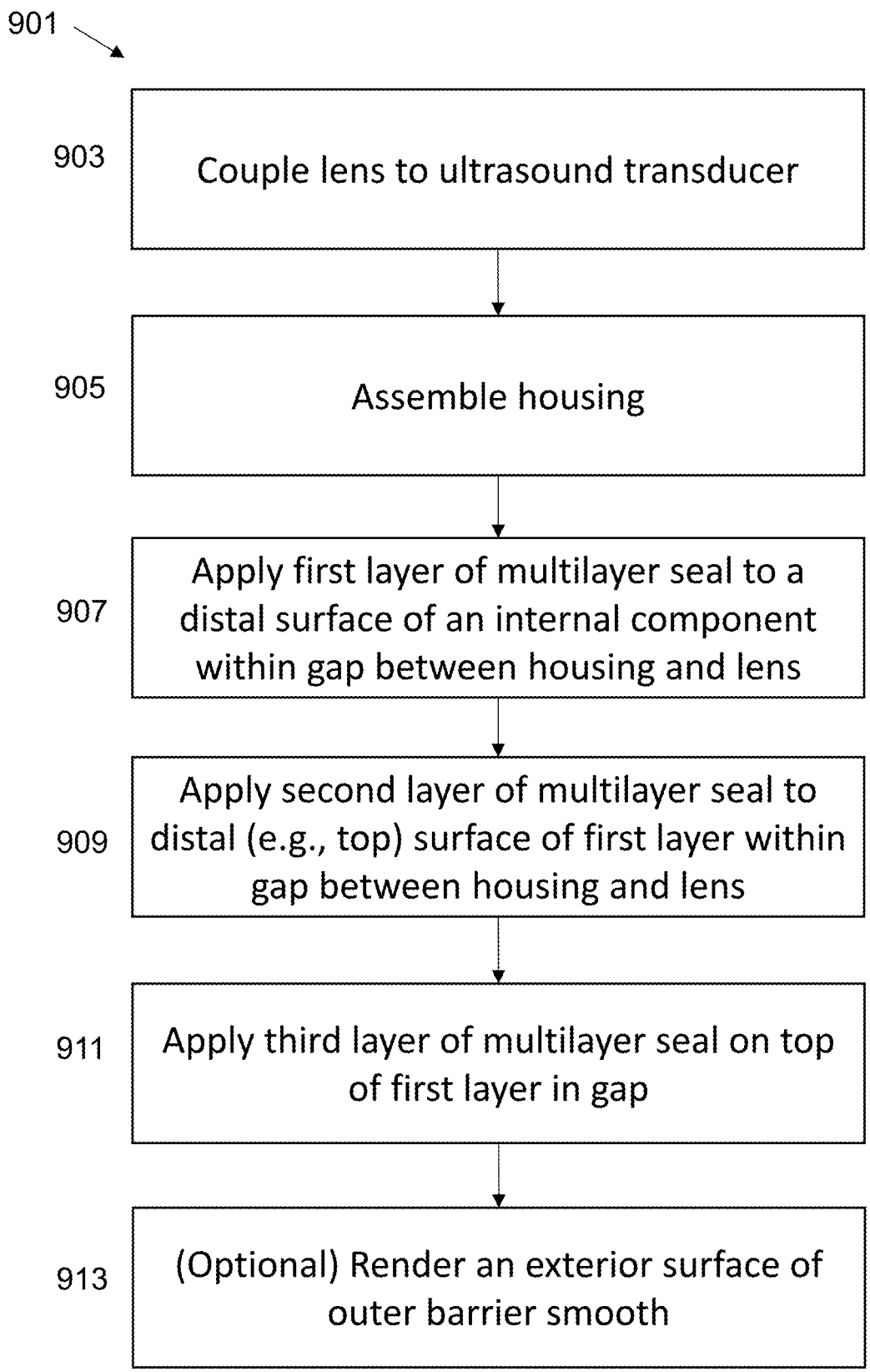
FIG. 9B shows steps of a method for fabrication of an outer barrier of an ultrasound device comprising a multilayer seal, in accordance with embodiments.

FIG. 9B shows an example of steps of a method 901 of fabricating an ultrasound system or device comprising a multilayer seal. In some cases, a lens 222 can be coupled to one or more internal components (e.g., such as an ultrasound transducer) of the ultrasound device (e.g., wherein the lens 222 is directly or indirectly coupled to the one or more internal components of the ultrasound device) (e.g., as shown in step 903). In some cases, a housing can be assembled (e.g., partially) around the coupled lens and internal component(s) (e.g., as shown in step 905). A first layer 242 of the multilayer seal 240 (e.g., an adhesive, thixotropic first layer comprising an indicator material) can be applied to an interior surface (e.g., a distal surface of an internal component) of a gap 301 between the housing 231 and the lens 222, for example, by using a needle (e.g., a dispensing needle) to dispense the first layer 242 onto the interior surface (e.g., wherein the first layer 242 is applied such that it is in contact with the entirety of a perimeter of a side wall of the housing 231, in contact with the entirety of a perimeter of a side wall of the lens 222, and in contact with the entire distal surface of the interior surface), for example, as shown in step 907. In some cases, a second layer 244 of the multilayer seal 240 can be applied to a distal surface of the first layer 242 of the multilayer seal 240 (e.g., wherein the second layer 244 is applied such that it is in contact with the entirety of a perimeter of a side wall of the housing 231, in contact with the entirety of a perimeter of a side wall of the lens 222, and in contact with the entire distal surface of the first layer 242) after the first layer 242 has been applied within the gap 301 (e.g., as shown in step 909). In some cases, a third layer 246 (e.g., an adhesive third layer, which may comprise the same material(s) as the second layer 244 in the same or different proportions as the second layer) can be applied to a distal surface of the first layer within the gap 301 (e.g., wherein the third layer 246 is applied such that it is in contact with the entirety of a perimeter of a side wall of the housing 231, in contact with the entirety of a perimeter of a side wall of the lens 222, and in contact with the entire distal surface of the first layer 242), for example, as shown in step 911 of FIG. 9B. In some cases, the exterior (e.g., distal) surface of the third layer 246 can be rendered smooth, e.g., by cutting, grinding, or polishing the distal surface of the third layer 246 until an angle of a tangent of the third layer 246 matches (or approximately matches, e.g., within 10% or within 25%) the angle of a tangent of the lens 222 at a first interface 251 and/or until an angle of a tangent of the distal surface of the third layer 246 matches (or approximately matches, e.g., within 10% or within 25%) the angle of a tangent of a distal surface of the housing 231 at a second interface 252 (e.g., as shown in step 913 of FIG. 9B).

In some cases, all or a portion of a layer (e.g., a first layer, a second layer, or a third layer) of a multilayer seal can be fabricated or applied to a surface or in a gap of an ultrasound system or device using a needle, such as a dispensing needle (e.g., with a syringe or pump). In some cases, all or a portion of a layer (e.g., a first layer, a second layer, or a third layer) of a multilayer seal can be applied using needle (e.g., a dispensing needle) oriented at a low angle relative to the surface on which it is deposited, e.g., to allow deposition of a flatter, continuous bead of layer material. This can be especially advantageous for deposition of thixotropic materials, which may retain an uneven surface if applied too quickly or using a high needle angle. In some cases, adding an additional layer (e.g., a third layer) comprising a self-leveling material on top of a layer comprising a thixotropic material (e.g., a first layer and/or a second layer) can aid in establishing a smooth or flat external surface of the outer barrier comprising the multilayer seal 240 (e.g., as shown in FIG. 5).

Liquids

Ultrasound devices (e.g., a distal surface of an outer barrier of an ultrasound probe head) may be placed in direct contact with one or more liquids during or between uses of the ultrasound devices. In some cases, contacting a liquid to a surface (e.g., all or a portion of a distal surface of an outer surface) of an ultrasound device can present a risk of the liquid traversing the outer barrier of the ultrasound device to an interior compartment of the ultrasound device. In some cases, a liquid that has traversed an outer barrier of an ultrasound device can adversely affect the function of one or more internal components (e.g., an ultrasound transducer, a MEMS array, circuitry of a printed circuit board (PCB) or ASIC of the device, which may include a processor or a memory) or of the ultrasound device as a whole. In some cases, the precision or accuracy of the ultrasound can be adversely affected if one or more internal components of an ultrasound device or system is contacted by a liquid (e.g., which has traversed an outer barrier of the device or system). In some cases, one or more internal components of an ultrasound device or system can be damaged or destroyed as a result of being contacted by a liquid (e.g., which has traversed an outer barrier of the device or system). In some cases, an outer barrier of an ultrasound device or system can or must be placed into contact with a liquid (e.g., an acoustic medium or a bodily fluid) during use of the device or system (e.g., to improve acoustic energy transmission and/or to access regions of a patient's body to be assayed with the ultrasound device or system). In some cases, an outer barrier of an ultrasound device or system can or must be placed into contact with a liquid (e.g., a disinfectant or rinse solution) between uses of the device or system (e.g., to disinfect or sterilize the device or system, for instance, to prevent transfer of one or more pathogens to a subsequent patient). In some cases, an outer barrier of an ultrasound device or system can or must be brought into contact with a liquid repeatedly (e.g., over the course of multiple instances of exposure to liquids during use and/or disinfection between uses) over the lifespan of the ultrasound device or system. In some cases, an outer barrier of an ultrasound device or system can or must be brought into contact with a liquid for a prolonged period of time (e.g., during use and/or during disinfection). In some cases, such repeated direct contact with a liquid can lead to or increase the risk of liquid intrusion into an interior of the ultrasound system or device, which may cause or increase the likelihood of damage to one or more interior components of the ultrasound system or device (e.g., as a result of short circuiting, chemical reactions, fracture of mechanical MEMS membranes, fracture of electrical connections, and/or unintended modulation of acoustic impedance within an acoustic pathway of the device, for example as a result of condensation or clouding). In some cases, prolonged contact with a liquid (e.g., submerging all or a portion of an ultrasound device or system in a liquid, for instance, during treatment of the device or system with a high-level disinfectant) can lead to or increase the risk of liquid intrusion into an interior of the ultrasound system or device, which may cause or increase the likelihood of damage to one or more interior components of the ultrasound system or device (e.g., as a result of short circuiting, chemical reactions, fracture of mechanical MEMS membranes, fracture of electrical connections, and/or unintended modulation of acoustic impedance within an acoustic pathway of the device, for example as a result of condensation or clouding). In some cases, an outer barrier of an ultrasound system or device comprising a multilayer seal 240 described herein can reduce a likelihood of or prevent liquid intrusion into an interior compartment of an ultrasound system or device, for example, even when contact with a liquid is prolonged or if the liquid is water-based or alcohol-based.

A liquid can comprise water or a water-based (e.g., aqueous) substance. In some cases, a liquid can comprise an ultrasound gel (e.g., an acoustic gel). In some cases, an ultrasound gel can comprise water, a polyol (e.g., propane-1,2,3-triol, or glycerin), a glycol ether (e.g., 2-phenoxyethan-1-ol, or phenoxyethanol), propylene glycol (e.g., propane-1,2-diol), and/or a petroleum-based substance, such as a synthetic dye. In some cases, use of an ultrasound device can comprise contacting an exterior surface of an ultrasound device with an imaging medium, such as an acoustic gel, which may be a water-based material. In some cases, a liquid can comprise a saline solution (e.g., normal saline, which can comprise exactly or approximately 0.90% w/v of sodium chloride in water or lactated Ringer's solution, which can comprise sodium chloride, sodium lactate, potassium chloride, and/or calcium chloride in water). In some cases, a liquid can comprise a bodily fluid. In some cases, use of an ultrasound device can comprise contacting an exterior surface of an ultrasound with a bodily fluid. In some cases, water molecules (e.g., alone or in combination with a component of an aqueous solution) can cause a color change in an indicator material (e.g., of a first layer 242 of a multilayer seal 240), e.g., after contacting the indicator material. In some cases, a solute or compound (e.g., an inorganic compound, an organic compound, or a biological substance, such as a protein, an enzyme, a lipid, or nucleic acid) mixed with water in an aqueous solution (e.g., alone or in combination with water) can cause a color change in an indicator material (e.g., of a first layer 242 of a multilayer seal 240), e.g., after contacting the indicator material.

A liquid can comprise a disinfectant. In some cases, a disinfectant can comprise an organic compound (e.g., an alcohol or an aldehyde). In some cases, a disinfectant can comprise an inorganic compound (e.g., a chlorine, a hypochlorite, a hypochlorous acid, a hydroxide, or an iodide). In some cases, a disinfectant can be water-based (e.g., an aqueous solution). In some cases, a disinfectant can comprise an alcohol (e.g., ethyl alcohol, isopropyl alcohol, or a combination thereof). In some cases, a disinfectant can comprise an aldehyde. For example, a disinfectant can comprise formaldehyde, glutaraldehyde, or phthalaldehyde (e.g., ortho-phthaladehyde (OPA, or o-phthalaldehyde)). In some cases, a disinfectant can comprise an oxidizing agent, such as hydrogen peroxide. In some cases, a disinfectant can comprise an ammonium-based compound, such as a quaternary ammonium cation. In some cases, a disinfectant can comprise chlorine, hypochlorite (e.g., sodium hypochlorite or calcium hypochlorite), or hypochlorous acid (e.g., in an aqueous solution). In some cases, a disinfectant can comprise a phenolic, such as phenol, thymol, o-phenylphenol, or chloroxylenol. In some cases, a disinfectant can be an enzymatic cleaner (e.g., comprising an enzyme). In some cases, water molecules of a disinfectant (e.g., alone or in combination with a component of an aqueous solution) can cause a color change in an indicator material (e.g., of a first layer 242 of a multilayer seal 240), e.g., after the disinfectant contacts the indicator material. In some cases, a solute or compound of a disinfectant (e.g., an inorganic compound or an organic compound, such as a protein, an enzyme, a lipid, or nucleic acid) can cause a color change in an indicator material (e.g., of a first layer 242 of a multilayer seal 240), e.g., after contacting the indicator material.

In some cases, disinfection of ultrasound equipment can involve low-level disinfection, which can comprise application of a disinfectant (e.g., using disinfectant wipes) to an outer surface of an ultrasound device or a component of an ultrasound system, such as an ultrasound probe head, prior to, after, or between uses. In some cases, a low-level disinfectant can comprise a compound comprising ammonium (e.g., a quaternary ammonium compound). In some cases, ultrasound devices and systems must be subjected to high-level disinfection. High-level disinfection of an exterior surface of an ultrasound system or device can comprise contacting the exterior surface of the ultrasound device (e.g., an exterior surface of an outer barrier of the ultrasound device) with a liquid (e.g., a high-level disinfectant) for an extended period of time. In some cases, high-level disinfection of a surface of an ultrasound system or device (e.g., all or a portion of an exterior surface, such as an outer barrier, which may comprise a multilayer seal) can involve contacting the surface of the ultrasound system or device with a liquid (e.g., a disinfectant) for a longer period of time than during a low-level disinfection process. For example, high-level disinfection of a surface of an ultrasound system or device can comprise contacting all or a portion of the surface with a liquid (e.g., a disinfectant, such as phthalaldehyde) for a period from 20 minutes to 1 hour, from 1 hour to 2 hours, from 2 hours to 3 hours, from 3 hours to 4 hours, from 4 hours to 6 hours, from 6 hours to 12 hours, from 12 hours to 24 hours, or more than 24 hours. In some cases, low-level disinfection of a surface of an ultrasound system or device can comprise contacting all or a portion of the surface with a liquid (e.g., a disinfectant, such as a quaternary ammonium compound) for a period for less than 5 minutes, from 5 minutes to 10 minutes, from 10 minutes to 20 minutes, from 20 minutes to 1 hour, from 1 hour to 2 hours, or more than 2 hours.

In some cases, all or a portion of an outer barrier (e.g., comprising an external surface) of an ultrasound system or device can be placed in contact with a liquid for 0.1 hours to 24 hours. In some cases, all or a portion of an outer barrier (e.g., comprising an external surface) of an ultrasound system or device can be placed in contact with a liquid for 0.1 hours to 0.2 hours, 0.1 hours to 0.4 hours, 0.1 hours to 0.5 hours, 0.1 hours to 0.8 hours, 0.1 hours to 1 hour, 0.1 hours to 2 hours, 0.1 hours to 3 hours, 0.1 hours to 4 hours, 0.1 hours to 6 hours, 0.1 hours to 12 hours, 0.1 hours to 24 hours, 0.2 hours to 0.4 hours, 0.2 hours to 0.5 hours, 0.2 hours to 0.8 hours, 0.2 hours to 1 hour, 0.2 hours to 2 hours, 0.2 hours to 3 hours, 0.2 hours to 4 hours, 0.2 hours to 6 hours, 0.2 hours to 12 hours, 0.2 hours to 24 hours, 0.4 hours to 0.5 hours, 0.4 hours to 0.8 hours, 0.4 hours to 1 hour, 0.4 hours to 2 hours, 0.4 hours to 3 hours, 0.4 hours to 4 hours, 0.4 hours to 6 hours, 0.4 hours to 12 hours, 0.4 hours to 24 hours, 0.5 hours to 0.8 hours, 0.5 hours to 1 hour, 0.5 hours to 2 hours, 0.5 hours to 3 hours, 0.5 hours to 4 hours, 0.5 hours to 6 hours, 0.5 hours to 12 hours, 0.5 hours to 24 hours, 0.8 hours to 1 hour, 0.8 hours to 2 hours, 0.8 hours to 3 hours, 0.8 hours to 4 hours, 0.8 hours to 6 hours, 0.8 hours to 12 hours, 0.8 hours to 24 hours, 1 hour to 2 hours, 1 hour to 3 hours, 1 hour to 4 hours, 1 hour to 6 hours, 1 hour to 12 hours, 1 hour to 24 hours, 2 hours to 3 hours, 2 hours to 4 hours, 2 hours to 6 hours, 2 hours to 12 hours, 2 hours to 24 hours, 3 hours to 4 hours, 3 hours to 6 hours, 3 hours to 12 hours, 3 hours to 24 hours, 4 hours to 6 hours, 4 hours to 12 hours, 4 hours to 24 hours, 6 hours to 12 hours, 6 hours to 24 hours, or 12 hours to 24 hours. In some cases, all or a portion of an outer barrier (e.g., comprising an external surface) of an ultrasound system or device can be placed in contact with a liquid for 0.1 hours, 0.2 hours, 0.4 hours, 0.5 hours, 0.8 hours, 1 hour, 2 hours, 3 hours, 4 hours, 6 hours, 12 hours, or 24 hours. In some cases, all or a portion of an outer barrier (e.g., comprising an external surface) of an ultrasound system or device can be placed in contact with a liquid for at least 0.1 hours, 0.2 hours, 0.4 hours, 0.5 hours, 0.8 hours, 1 hour, 2 hours, 3 hours, 4 hours, 6 hours, or 12 hours. In some cases, all or a portion of an outer barrier (e.g., comprising an external surface) of an ultrasound system or device can be placed in contact with a liquid for at most 0.2 hours, 0.4 hours, 0.5 hours, 0.8 hours, 1 hour, 2 hours, 3 hours, 4 hours, 6 hours, 12 hours, or 24 hours.

In some cases, a multilayer seal can reduce the risk of liquid intrusion in an ultrasound system or device wherein the system or device has been in contact with a liquid for 0.1 hours to 24 hours. In some cases, a multilayer seal can reduce the risk of liquid intrusion in an ultrasound system or device wherein the system or device has been in contact with a liquid for 0.1 hours to 0.2 hours, 0.1 hours to 0.4 hours, 0.1 hours to 0.5 hours, 0.1 hours to 0.8 hours, 0.1 hours to 1 hour, 0.1 hours to 2 hours, 0.1 hours to 3 hours, 0.1 hours to 4 hours, 0.1 hours to 6 hours, 0.1 hours to 12 hours, 0.1 hours to 24 hours, 0.2 hours to 0.4 hours, 0.2 hours to 0.5 hours, 0.2 hours to 0.8 hours, 0.2 hours to 1 hour, 0.2 hours to 2 hours, 0.2 hours to 3 hours, 0.2 hours to 4 hours, 0.2 hours to 6 hours, 0.2 hours to 12 hours, 0.2 hours to 24 hours, 0.4 hours to 0.5 hours, 0.4 hours to 0.8 hours, 0.4 hours to 1 hour, 0.4 hours to 2 hours, 0.4 hours to 3 hours, 0.4 hours to 4 hours, 0.4 hours to 6 hours, 0.4 hours to 12 hours, 0.4 hours to 24 hours, 0.5 hours to 0.8 hours, 0.5 hours to 1 hour, 0.5 hours to 2 hours, 0.5 hours to 3 hours, 0.5 hours to 4 hours, 0.5 hours to 6 hours, 0.5 hours to 12 hours, 0.5 hours to 24 hours, 0.8 hours to 1 hour, 0.8 hours to 2 hours, 0.8 hours to 3 hours, 0.8 hours to 4 hours, 0.8 hours to 6 hours, 0.8 hours to 12 hours, 0.8 hours to 24 hours, 1 hour to 2 hours, 1 hour to 3 hours, 1 hour to 4 hours, 1 hour to 6 hours, 1 hour to 12 hours, 1 hour to 24 hours, 2 hours to 3 hours, 2 hours to 4 hours, 2 hours to 6 hours, 2 hours to 12 hours, 2 hours to 24 hours, 3 hours to 4 hours, 3 hours to 6 hours, 3 hours to 12 hours, 3 hours to 24 hours, 4 hours to 6 hours, 4 hours to 12 hours, 4 hours to 24 hours, 6 hours to 12 hours, 6 hours to 24 hours, or 12 hours to 24 hours. In some cases, a multilayer seal can reduce the risk of liquid intrusion in an ultrasound system or device wherein the system or device has been in contact with a liquid for 0.1 hours, 0.2 hours, 0.4 hours, 0.5 hours, 0.8 hours, 1 hour, 2 hours, 3 hours, 4 hours, 6 hours, 12 hours, or 24 hours. In some cases, a multilayer seal can reduce the risk of liquid intrusion in an ultrasound system or device wherein the system or device has been in contact with a liquid for at least 0.1 hours, 0.2 hours, 0.4 hours, 0.5 hours, 0.8 hours, 1 hour, 2 hours, 3 hours, 4 hours, 6 hours, 12 hours, or 24 hours. In some cases, a multilayer seal can reduce the risk of liquid intrusion in an ultrasound system or device wherein the system or device has been in contact with a liquid for at most 0.1 hours, 0.2 hours, 0.4 hours, 0.5 hours, 0.8 hours, 1 hour, 2 hours, 3 hours, 4 hours, 6 hours, 12 hours, or 24 hours.

In some cases, a method of disinfecting an ultrasound system or device can comprise contacting all or a portion of an outer barrier of the system or device with a liquid (e.g., a disinfectant, such as a low-level disinfectant) for 0.1 hours to 48 hours. In some cases, a method of disinfecting an ultrasound system or device can comprise contacting all or a portion of an outer barrier of the system or device with a liquid (e.g., a disinfectant, such as a low-level disinfectant) for 0.1 hours to 0.5 hours, 0.1 hours to 1 hour, 0.1 hours to 2 hours, 0.1 hours to 4 hours, 0.1 hours to 6 hours, 0.1 hours to 8 hours, 0.1 hours to 12 hours, 0.1 hours to 24 hours, 0.1 hours to 36 hours, 0.1 hours to 48 hours, 0.5 hours to 1 hour, 0.5 hours to 2 hours, 0.5 hours to 4 hours, 0.5 hours to 6 hours, 0.5 hours to 8 hours, 0.5 hours to 12 hours, 0.5 hours to 24 hours, 0.5 hours to 36 hours, 0.5 hours to 48 hours, 1 hour to 2 hours, 1 hour to 4 hours, 1 hour to 6 hours, 1 hour to 8 hours, 1 hour to 12 hours, 1 hour to 24 hours, 1 hour to 36 hours, 1 hour to 48 hours, 2 hours to 4 hours, 2 hours to 6 hours, 2 hours to 8 hours, 2 hours to 12 hours, 2 hours to 24 hours, 2 hours to 36 hours, 2 hours to 48 hours, 4 hours to 6 hours, 4 hours to 8 hours, 4 hours to 12 hours, 4 hours to 24 hours, 4 hours to 36 hours, 4 hours to 48 hours, 6 hours to 8 hours, 6 hours to 12 hours, 6 hours to 24 hours, 6 hours to 36 hours, 6 hours to 48 hours, 8 hours to 12 hours, 8 hours to 24 hours, 8 hours to 36 hours, 8 hours to 48 hours, 12 hours to 24 hours, 12 hours to 36 hours, 12 hours to 48 hours, 24 hours to 36 hours, 24 hours to 48 hours, or 36 hours to 48 hours. In some cases, a method of disinfecting an ultrasound system or device can comprise contacting all or a portion of an outer barrier of the system or device with a liquid (e.g., a disinfectant, such as a low-level disinfectant) for 0.1 hours, 0.5 hours, 1 hour, 2 hours, 4 hours, 6 hours, 8 hours, 12 hours, 24 hours, 36 hours, or 48 hours. In some cases, a method of disinfecting an ultrasound system or device can comprise contacting all or a portion of an outer barrier of the system or device with a liquid (e.g., a disinfectant, such as a low-level disinfectant) for at least 0.1 hours, 0.5 hours, 1 hour, 2 hours, 4 hours, 6 hours, 8 hours, 12 hours, 24 hours, 36 hours, or 48 hours. In some cases, a method of disinfecting an ultrasound system or device can comprise contacting all or a portion of an outer barrier of the system or device with a liquid (e.g., a disinfectant, such as a low-level disinfectant) for at most 0.1 hours, 0.5 hours, 1 hour, 2 hours, 4 hours, 6 hours, 8 hours, 12 hours, 24 hours, 36 hours, or 48 hours.

In some cases, a method of disinfecting an ultrasound system or device can comprise contacting all or a portion of an outer barrier of the system or device with a liquid (e.g., a disinfectant, such as a high-level disinfectant) for 0.1 hours to 48 hours. In some cases, a method of disinfecting an ultrasound system or device can comprise contacting all or a portion of an outer barrier of the system or device with a liquid (e.g., a disinfectant, such as a high-level disinfectant) for 0.1 hours to 0.5 hours, 0.1 hours to 1 hour, 0.1 hours to 2 hours, 0.1 hours to 4 hours, 0.1 hours to 6 hours, 0.1 hours to 8 hours, 0.1 hours to 12 hours, 0.1 hours to 24 hours, 0.1 hours to 36 hours, 0.1 hours to 48 hours, 0.5 hours to 1 hour, 0.5 hours to 2 hours, 0.5 hours to 4 hours, 0.5 hours to 6 hours, 0.5 hours to 8 hours, 0.5 hours to 12 hours, 0.5 hours to 24 hours, 0.5 hours to 36 hours, 0.5 hours to 48 hours, 1 hour to 2 hours, 1 hour to 4 hours, 1 hour to 6 hours, 1 hour to 8 hours, 1 hour to 12 hours, 1 hour to 24 hours, 1 hour to 36 hours, 1 hour to 48 hours, 2 hours to 4 hours, 2 hours to 6 hours, 2 hours to 8 hours, 2 hours to 12 hours, 2 hours to 24 hours, 2 hours to 36 hours, 2 hours to 48 hours, 4 hours to 6 hours, 4 hours to 8 hours, 4 hours to 12 hours, 4 hours to 24 hours, 4 hours to 36 hours, 4 hours to 48 hours, 6 hours to 8 hours, 6 hours to 12 hours, 6 hours to 24 hours, 6 hours to 36 hours, 6 hours to 48 hours, 8 hours to 12 hours, 8 hours to 24 hours, 8 hours to 36 hours, 8 hours to 48 hours, 12 hours to 24 hours, 12 hours to 36 hours, 12 hours to 48 hours, 24 hours to 36 hours, 24 hours to 48 hours, 36 hours to 48 hours, or 48 hours to 96 hours. In some cases, a method of disinfecting an ultrasound system or device can comprise contacting all or a portion of an outer barrier of the system or device with a liquid (e.g., a disinfectant, such as a high-level disinfectant) for 0.1 hours, 0.5 hours, 1 hour, 2 hours, 4 hours, 6 hours, 8 hours, 12 hours, 24 hours, 36 hours, 48 hours, 72 hours, or 96 hours. In some cases, a method of disinfecting an ultrasound system or device can comprise contacting all or a portion of an outer barrier of the system or device with a liquid (e.g., a disinfectant, such as a high-level disinfectant) for at least 0.1 hours, 0.5 hours, 1 hour, 2 hours, 4 hours, 6 hours, 8 hours, 12 hours, 24 hours, 36 hours, 48 hours, 72 hours, or 96 hours. In some cases, a method of disinfecting an ultrasound system or device can comprise contacting all or a portion of an outer barrier of the system or device with a liquid (e.g., a disinfectant, such as a high-level disinfectant) for at most 0.1 hours, 0.5 hours, 1 hour, 2 hours, 4 hours, 6 hours, 8 hours, 12 hours, 24 hours, 36 hours, 48 hours, 72 hours, or 96 hours.

In some cases, an indicator material of a multilayer seal 240 can undergo a color change when placed in contact (e.g., direct contact) with a liquid (e.g., water, a disinfectant, or a bodily fluid) for 0.1 hours to 24 hours. In some cases, an indicator material of a multilayer seal 240 can undergo a color change when placed in contact (e.g., direct contact) with a liquid (e.g., water, a disinfectant, or a bodily fluid) for 0.1 hours to 0.2 hours, 0.1 hours to 0.4 hours, 0.1 hours to 0.5 hours, 0.1 hours to 0.8 hours, 0.1 hours to 1 hour, 0.1 hours to 2 hours, 0.1 hours to 3 hours, 0.1 hours to 4 hours, 0.1 hours to 6 hours, 0.1 hours to 12 hours, 0.1 hours to 24 hours, 0.2 hours to 0.4 hours, 0.2 hours to 0.5 hours, 0.2 hours to 0.8 hours, 0.2 hours to 1 hour, 0.2 hours to 2 hours, 0.2 hours to 3 hours, 0.2 hours to 4 hours, 0.2 hours to 6 hours, 0.2 hours to 12 hours, 0.2 hours to 24 hours, 0.4 hours to 0.5 hours, 0.4 hours to 0.8 hours, 0.4 hours to 1 hour, 0.4 hours to 2 hours, 0.4 hours to 3 hours, 0.4 hours to 4 hours, 0.4 hours to 6 hours, 0.4 hours to 12 hours, 0.4 hours to 24 hours, 0.5 hours to 0.8 hours, 0.5 hours to 1 hour, 0.5 hours to 2 hours, 0.5 hours to 3 hours, 0.5 hours to 4 hours, 0.5 hours to 6 hours, 0.5 hours to 12 hours, 0.5 hours to 24 hours, 0.8 hours to 1 hour, 0.8 hours to 2 hours, 0.8 hours to 3 hours, 0.8 hours to 4 hours, 0.8 hours to 6 hours, 0.8 hours to 12 hours, 0.8 hours to 24 hours, 1 hour to 2 hours, 1 hour to 3 hours, 1 hour to 4 hours, 1 hour to 6 hours, 1 hour to 12 hours, 1 hour to 24 hours, 2 hours to 3 hours, 2 hours to 4 hours, 2 hours to 6 hours, 2 hours to 12 hours, 2 hours to 24 hours, 3 hours to 4 hours, 3 hours to 6 hours, 3 hours to 12 hours, 3 hours to 24 hours, 4 hours to 6 hours, 4 hours to 12 hours, 4 hours to 24 hours, 6 hours to 12 hours, 6 hours to 24 hours, or 12 hours to 24 hours. In some cases, an indicator material of a multilayer seal 240 can undergo a color change when placed in contact (e.g., direct contact) with a liquid (e.g., water, a disinfectant, or a bodily fluid) for 0.1 hours, 0.2 hours, 0.4 hours, 0.5 hours, 0.8 hours, 1 hour, 2 hours, 3 hours, 4 hours, 6 hours, 12 hours, or 24 hours. In some cases, an indicator material of a multilayer seal 240 can undergo a color change when placed in contact (e.g., direct contact) with a liquid (e.g., water, a disinfectant, or a bodily fluid) for at least 0.1 hours, 0.2 hours, 0.4 hours, 0.5 hours, 0.8 hours, 1 hour, 2 hours, 3 hours, 4 hours, 6 hours, 12 hours, or 24 hours. In some cases, an indicator material of a multilayer seal 240 can undergo a color change when placed in contact (e.g., direct contact) with a liquid (e.g., water, a disinfectant, or a bodily fluid) for at most 0.1 hours, 0.2 hours, 0.4 hours, 0.5 hours, 0.8 hours, 1 hour, 2 hours, 3 hours, 4 hours, 6 hours, 12 hours, or 24 hours.

Ultrasound Transducers

In some cases, systems, devices, or methods described herein can comprise one or more ultrasound transducers (e.g., ultrasonic transducers). In some cases, an ultrasound transducer comprises a wafer, which may comprise a printed circuit board (PCB). In many cases, the one or more ultrasound transducers (e.g., and one or more other internal components, such as a MEMS array, a MEMS wafer, an ASIC, heat management components, and/or a processor) of an ultrasound system or device can be located within an internal compartment (e.g., internal space) of the ultrasound system or device. In some cases, an internal compartment or space of an ultrasound system can be surrounded by (e.g., spatially encompassed by) an outer barrier, which can comprise a housing 231, a multilayer seal 240, and/or a lens 222. In some cases, an internal compartment or space of an ultrasound system can be defined by an outer barrier surrounding (e.g., spatially encompassing) it. In some cases, systems, devices, or methods described herein can comprise piezoelectric micromachine ultrasound transducers (pMUTs). In some cases, system, devices, or methods described herein can comprise one or more capacitive micromachine ultrasonic transducers (cMUTs). Piezoelectric micromachine ultrasound transducers (pMUTs) can be formed on a substrate, such as a semiconductor wafer (e.g., a printed circuit board, PCB). pMUT elements constructed on semiconductor substrates can offer a smaller size profile than bulky conventional transducers having bulkier piezoelectrical material. In some cases, pMUTs can also be less expensive to manufacture and/or may allow less complicated and higher performance interconnection between the transducers and additional electronics of the ultrasound device or system.

Micromachine ultrasound transducers (MUTs), which can include pMUTs and/or cMUTs can include a diaphragm (e.g., a thin membrane attached, for example at the membrane edges, to one or more portions of the interior of an imaging device (e.g., ultrasound probe). In contrast, traditional bulk piezoelectric (PZT) elements typically consist of a single solid piece of material. Such traditional PZT ultrasound systems and devices can be expensive to fabricate, for example, because great precision is required to cut and mount PZT or ceramic material comprising the PZT ultrasound systems and devices with the proper spacing. Additionally, traditional PZT ultrasound systems and devices can have significantly higher transducer impedance compared to the impedance of the transmit/receive electronics of the PZT systems and devices, which can adversely affect performance.

In some cases, one or more transducer elements can be configured to transmit and/or receive signals at a specific frequency or bandwidth (e.g., wherein the bandwidth is associated with a center frequency). In some cases, one or more transducer elements can be further configured to transmit and/or receive signals at additional center frequencies and bandwidths. Such multi-frequency transducer elements can be referred to as multi-modal elements, and can, in some embodiments, be used to expand a bandwidth of an imaging system or device 100. A transducer element or pixel can be configured to emit (e.g., transmit) and/or receive an ultrasonic energy (e.g., an ultrasonic waveform, pattern, or pressure wave) at a suitable center frequency, e.g., from 0.1 megahertz (MHz) to 100 MHz. In some cases, a transducer or pixel can be configured to transmit or receive ultrasonic energy at a center frequency of 0.1 MHz to 1 MHz, 0.1 MHz to 1.8 MHz, 0.1 MHz to 3.5 MHz, 0.1 MHz to 5.1 MHz, 0.1 MHz to 10 MHz, 0.1 MHz to 25 MHz, 0.1 MHz to 50 MHz, 0.1 MHz to 100 MHz, 1 MHz to 1.8 MHz, 1 MHz to 3.5 MHz, 1 MHz to 5.1 MHz, 1 MHz to 10 MHz, 1 MHz to 25 MHz, 1 MHz to 50 MHz, 1 MHz to 100 MHz, 1.8 MHz to 3.5 MHz, 1.8 MHz to 5.1 MHz, 1.8 MHz to 10 MHz, 1.8 MHz to 25 MHz, 1.8 MHz to 50 MHz, 1.8 MHz to 100 MHz, 3.5 MHz to 5.1 MHz, 3.5 MHz to 10 MHz, 3.5 MHz to 25 MHz, 3.5 MHz to 50 MHz, 3.5 MHz to 100 MHz, 5.1 MHz to 10 MHz, 5.1 MHz to 25 MHz, 5.1 MHz to 50 MHz, 5.1 MHz to 100 MHz, 10 MHz to 25 MHz, 10 MHz to 50 MHz, 10 MHz to 100 MHz, 25 MHz to 50 MHz, 25 MHz to 100 MHz, or 50 MHz to 100 MHz. In some cases, a transducer or pixel can be configured to transmit or receive ultrasonic energy at a center frequency of 0.1 MHz, 1 MHz, 1.8 MHz, 3.5 MHz, 5.1 MHz, 10 MHz, 25 MHz, 50 MHz, or 100 MHz. In some cases, a transducer or pixel can be configured to transmit or receive ultrasonic energy at a center frequency of at least 0.1 MHz, 1 MHz, 1.8 MHz, 3.5 MHz, 5.1 MHz, 10 MHz, 25 MHz, 50 MHz, or 100 MHz. In some cases, a transducer or pixel can be configured to transmit or receive ultrasonic energy at a center frequency of at most 0.1 MHz, 1 MHz, 1.8 MHz, 3.5 MHz, 5.1 MHz, 10 MHz, 25 MHz, 50 MHz, or 100 MHz.

Computing System

Figure 10:
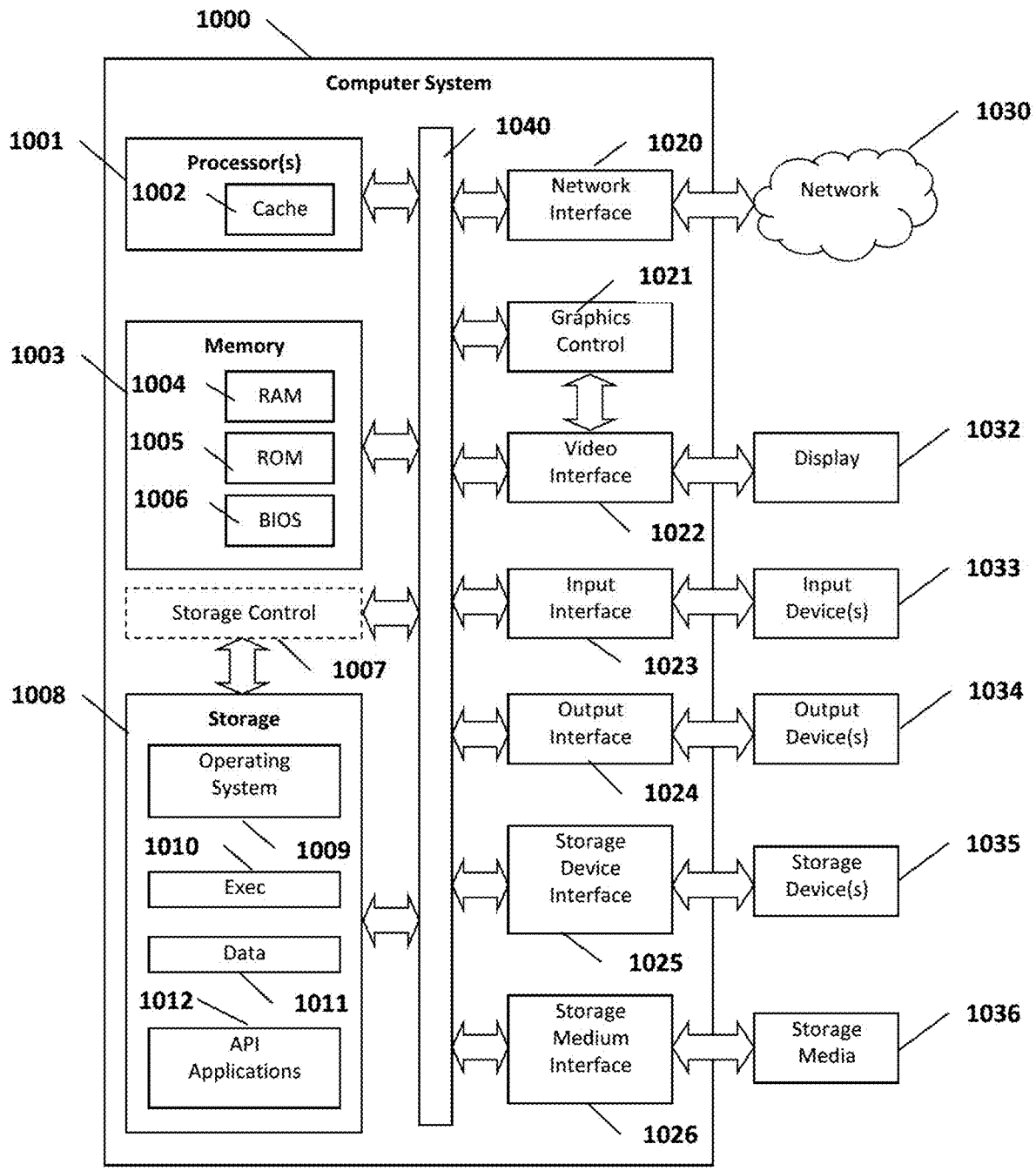
FIG. 10 shows a schematic diagram of a computer system, in accordance with embodiments.

An ultrasound system or device described herein can be comprise or interface with a computer system. FIG. 10 is a block diagram depicting an exemplary machine that includes a computer system 1000 (e.g., a processing or computing system) within which a set of instructions can execute for causing a device to perform or execute any one or more of the aspects and/or methodologies for static code scheduling of the present disclosure. The components in FIG. 10 are examples only and do not limit the scope of use or functionality of any hardware, software, embedded logic component, or a combination of two or more such components implementing particular embodiments.

Computer system 1000 may include one or more processors 1001, a memory 1003, and a storage 1008 that communicate with each other, and with other components, via a bus 1040. The bus 1040 may also link a display 1032, one or more input devices 1033 (which may, for example, include a keypad, a keyboard, a mouse, a stylus, etc.), one or more output devices 1034, one or more storage devices 1035, and various tangible storage media 1036. All of these elements may interface directly or via one or more interfaces or adaptors to the bus 1040. For instance, the various tangible storage media 1036 can interface with the bus 1040 via storage medium interface 1026. Computer system 1000 may have any suitable physical form, including but not limited to one or more integrated circuits (ICs), printed circuit boards (PCBs), mobile handheld devices (such as mobile telephones or PDAs), laptop or notebook computers, distributed computer systems, computing grids, or servers.

Computer system 1000 includes one or more processor(s) 1001 (e.g., central processing units (CPUs), general purpose graphics processing units (GPGPUs), or quantum processing units (QPUs)) that carry out functions. Processor(s) 1001 optionally contains a cache memory unit 1002 for temporary local storage of instructions, data, or computer addresses. Processor(s) 1001 are configured to assist in execution of computer readable instructions. Computer system 1000 may provide functionality for the components depicted in FIG. 10 as a result of the processor(s) 1001 executing non-transitory, processor-executable instructions embodied in one or more tangible computer-readable storage media, such as memory 1003, storage 1008, storage devices 1035, and/or storage medium 1036. The computer-readable media may store software that implements particular embodiments, and processor(s) 1001 may execute the software. Memory 1003 may read the software from one or more other computer-readable media (such as mass storage device(s) 1035, 1036) or from one or more other sources through a suitable interface, such as network interface 1020. The software may cause processor(s) 1001 to carry out one or more processes or one or more steps of one or more processes described or illustrated herein. Carrying out such processes or steps may include defining data structures stored in memory 1003 and modifying the data structures as directed by the software.

The memory 1003 may include various components (e.g., machine readable media) including, but not limited to, a random access memory component (e.g., RAM 1004) (e.g., static RAM (SRAM), dynamic RAM (DRAM), ferroelectric random access memory (FRAM), phase-change random access memory (PRAM), etc.), a read-only memory component (e.g., ROM 1005), and any combinations thereof. ROM 1005 may act to communicate data and instructions unidirectionally to processor(s) 1001, and RAM 1004 may act to communicate data and instructions bidirectionally with processor(s) 1001. ROM 1005 and RAM 1004 may include any suitable tangible computer-readable media described below. In one example, a basic input/output system 1006 (BIOS), including basic routines that help to transfer information between elements within computer system 1000, such as during start-up, may be stored in the memory 1003.

Fixed storage 1008 is connected bidirectionally to processor(s) 1001, optionally through storage control unit 1007. Fixed storage 1008 provides additional data storage capacity and may also include any suitable tangible computer-readable media described herein. Storage 1008 may be used to store operating system 1009, executable(s) 1010, data 1011, applications 1012 (application programs), and the like. Storage 1008 can also include an optical disk drive, a solid-state memory device (e.g., flash-based systems), or a combination of any of the above. Information in storage 1008 may, in appropriate cases, be incorporated as virtual memory in memory 1003.

In one example, storage device(s) 1035 may be removably interfaced with computer system 1000 (e.g., via an external port connector (not shown)) via a storage device interface 1025. Particularly, storage device(s) 1035 and an associated machine-readable medium may provide non-volatile and/or volatile storage of machine-readable instructions, data structures, program modules, and/or other data for the computer system 1000. In one example, software may reside, completely or partially, within a machine-readable medium on storage device(s) 1035. In another example, software may reside, completely or partially, within processor(s) 1001.

Bus 1040 connects a wide variety of subsystems. Herein, reference to a bus may encompass one or more digital signal lines serving a common function, where appropriate. Bus 1040 may be any of several types of bus structures including, but not limited to, a memory bus, a memory controller, a peripheral bus, a local bus, and any combinations thereof, using any of a variety of bus architectures. As an example and not by way of limitation, such architectures include an Industry Standard Architecture (ISA) bus, an Enhanced ISA (EISA) bus, a Micro Channel Architecture (MCA) bus, a Video Electronics Standards Association local bus (VLB), a Peripheral Component Interconnect (PCI) bus, a PCI-Express (PCI-X) bus, an Accelerated Graphics Port (AGP) bus, HyperTransport (HTX) bus, serial advanced technology attachment (SATA) bus, and any combinations thereof.

Computer system 1000 may also include an input device 1033. In one example, a user of computer system 1000 may enter commands and/or other information into computer system 1000 via input device(s) 1033. Examples of an input device(s) 1033 include, but are not limited to, an alpha-numeric input device (e.g., a keyboard), a pointing device (e.g., a mouse or touchpad), a touchpad, a touch screen, a multi-touch screen, a joystick, a stylus, a gamepad, an audio input device (e.g., a microphone, a voice response system, etc.), an optical scanner, a video or still image capture device (e.g., a camera), and any combinations thereof. In some embodiments, the input device is a Kinect, Leap Motion, or the like. Input device(s) 1033 may be interfaced to bus 1040 via any of a variety of input interfaces 1023 (e.g., input interface 1023) including, but not limited to, serial, parallel, game port, USB, FIREWIRE, THUNDERBOLT, or any combination of the above.

In particular embodiments, when computer system 1000 is connected to network 1030, computer system 1000 may communicate with other devices, specifically mobile devices and enterprise systems, distributed computing systems, cloud storage systems, cloud computing systems, and the like, connected to network 1030. Communications to and from computer system 1000 may be sent through network interface 1020. For example, network interface 1020 may receive incoming communications (such as requests or responses from other devices) in the form of one or more packets (such as Internet Protocol (IP) packets) from network 1030, and computer system 1000 may store the incoming communications in memory 1003 for processing. Computer system 100 may similarly store outgoing communications (such as requests or responses to other devices) in the form of one or more packets in memory 1003 and communicated to network 1030 from network interface 1020. Processor(s) 1001 may access these communication packets stored in memory 1003 for processing.

Examples of the network interface 1020 include, but are not limited to, a network interface card, a modem, and any combination thereof. Examples of a network 1030 or network segment 1030 include, but are not limited to, a distributed computing system, a cloud computing system, a wide area network (WAN) (e.g., the Internet, an enterprise network), a local area network (LAN) (e.g., a network associated with an office, a building, a campus or other relatively small geographic space), a telephone network, a direct connection between two computing devices, a peer-to-peer network, and any combinations thereof. A network, such as network 1030, may employ a wired and/or a wireless mode of communication. In general, any network topology may be used.

Information and data can be displayed through a display 1032. Examples of a display 1032 include, but are not limited to, a cathode ray tube (CRT), a liquid crystal display (LCD), a thin film transistor liquid crystal display (TFT-LCD), an organic liquid crystal display (OLED) such as a passive-matrix OLED (PMOLED) or active-matrix OLED (AMOLED) display, a plasma display, and any combinations thereof. The display 1032 can interface to the processor(s) 1001, memory 1003, and fixed storage 1008, as well as other devices, such as input device(s) 1033, via the bus 1040. The display 1032 is linked to the bus 1040 via a video interface 1022, and transport of data between the display 1032 and the bus 1040 can be controlled via the graphics control 1021. In some embodiments, the display is a video projector. In some embodiments, the display is a head-mounted display (HMD) such as a VR headset. In further embodiments, suitable VR headsets include, by way of non-limiting examples, HTC Vive, Oculus Rift, Samsung Gear VR, Microsoft HoloLens, Razer OSVR, FOVE VR, Zeiss VR One, Avegant Glyph, Freefly VR headset, and the like. In still further embodiments, the display is a combination of devices such as those disclosed herein.

In addition to a display 1032, computer system 1000 may include one or more other peripheral output devices 1034 including, but not limited to, an audio speaker, a printer, a storage device, and any combinations thereof. Such peripheral output devices may be connected to the bus 1040 via an output interface 1024. Examples of an output interface 1024 include, but are not limited to, a serial port, a parallel connection, a USB port, a FIREWIRE port, a THUNDERBOLT port, and any combinations thereof.

In addition or as an alternative, computer system 1000 may provide functionality as a result of logic hardwired or otherwise embodied in a circuit, which may operate in place of or together with software to execute one or more processes or one or more steps of one or more processes described or illustrated herein. Reference to software in this disclosure may encompass logic, and reference to logic may encompass software. Moreover, reference to a computer-readable medium may encompass a circuit (such as an IC) storing software for execution, a circuit embodying logic for execution, or both, where appropriate. The present disclosure encompasses any suitable combination of hardware, software, or both.

Those of skill in the art will appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by one or more processor(s), or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

In accordance with the description herein, suitable computing devices include, by way of non-limiting examples, server computers, desktop computers, laptop computers, notebook computers, handheld computers, Internet appliances, mobile smartphones, and tablet computers. Those of skill in the art will also recognize that select televisions, video players, and digital music players with optional computer network connectivity are suitable for use in the system described herein. Suitable tablet computers, in various embodiments, include those with booklet, slate, and convertible configurations, known to those of skill in the art.

In some embodiments, the computing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smartphone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

Applications

In some cases, an imaging system or device 100 described herein can be used in (e.g., non-invasive) medical imaging, lithotripsy, localized tissue heating for therapeutic interventions, highly intensive focused ultrasound (HIFU) surgery, and/or non-medical uses flow measurements in pipes (or speaker and microphone arrays). In some cases, an imaging system or device described herein can be used to determine direction and/or velocity of fluid flow (e.g., blood flow) in arteries and/or veins, for example using Doppler mode imaging. In some cases, an imaging system or device described herein can be used to measure tissue stiffness.

In some cases, an imaging system or device 100 described herein can be configured to perform one-dimensional imaging (e.g., A-Scan imaging). In some cases, an imaging system or device 100 described herein can be configured to perform two-dimensional imaging (e.g., B-Scan imaging). In some cases, an imaging system or device 100 described herein can be configured to perform three-dimensional imaging (e.g., C-Scan imaging). In some cases, an imaging system or device 100 described herein can be configured to perform Doppler imaging. In some cases, an imaging system or device 100 described herein may be switched to a different mode (e.g., between modes), including linear mode or sector mode. In some cases, an imaging system or device 100 can be electronically configured under program control (e.g., by a user).

In many cases, an imaging system or device 100 (e.g., a probe of an imaging system or device 100) can be portable. For instance, an imaging system or device 100 can comprise (e.g., house within a housing) a handheld casing, which can house one or more transducer elements, pixels, or arrays, ASICs, control circuitry, and/or a computing device. In some case, an imaging system or device 100 can comprise a battery.

Some Definitions

Unless otherwise defined, all technical terms used herein have the same meaning as commonly understood by one of ordinary skill in the art to which the present subject matter belongs.

As used in this specification and the appended claims, the singular forms "a," "an," and "the" include plural references unless the context clearly dictates otherwise. Any reference to "or" herein is intended to encompass "and/or" unless otherwise stated.

Reference throughout this specification to "some embodiments," "further embodiments," or "a particular embodiment," means that a particular feature, structure, or characteristic described in connection with the embodiment is included in at least one embodiment. Thus, the appearances of the phrase "in some embodiments," or "in further embodiments," or "in a particular embodiment" in various places throughout this specification are not necessarily all referring to the same embodiment. Furthermore, the particular features, structures, or characteristics may be combined in any suitable manner in one or more embodiments.

While preferred embodiments of the present subject matter have been shown and described herein, it will be obvious to those skilled in the art that such embodiments are provided by way of example only. Numerous variations, changes, and substitutions will now occur to those skilled in the art without departing from the present subject matter. It should be understood that various alternatives to the embodiments of the present subject matter described herein may be employed in practicing the present subject matter.

What is claimed is:

1. An ultrasound device comprising:
an outer barrier surrounding an ultrasound transducer, the outer barrier comprising:
a lens,
a housing, and
a multilayer seal in contact with the lens and the housing, wherein the multilayer seal comprises a first layer and a second layer, the first layer comprising an indicator material and the second layer comprising a first sealant, the second layer being disposed distal to the first layer relative to the ultrasound transducer.

2. The device of claim 1, wherein the multilayer seal further comprises a third layer, the third layer comprising a second sealant.

3. The device of claim 2, wherein the first sealant has a higher viscosity than the second sealant.

4. The device of claim 2, wherein the second sealant is a silicone-based sealant.

5. The device of claim 2, wherein the second sealant is an adhesive.

6. The device of claim 2, wherein the second layer is in contact with one or more of the housing, the lens, the entirety of a perimeter of the lens, or the entirety of a perimeter of an aperture of the housing.

7. The device of claim 2, wherein the third layer is disposed proximal to the first layer relative to the ultrasound transducer.

8. The device of claim 2, wherein the third layer is disposed distal to the first layer relative to the ultrasound transducer.

9. The device of claim 2, wherein the third layer is in contact with one or more of the entirety of a perimeter of the lens, the entirety of a perimeter of an aperture of the housing, or the entirety of a distal surface of the second layer.

10. The device of claim 2, wherein an interface of a distal surface of the third layer and a distal surface of the lens is one or more of smooth or flat.

11. The device of claim 2, wherein the indicator material is disposed between the second layer and the third layer.

12. The device of claim 1, wherein the first sealant comprises one or more of a thixotropic material or a silicone-based sealant.

13. The device of claim 1, wherein the outer barrier is impermeable to liquids.

14. The device of claim 1, wherein the first sealant is an adhesive.

15. The device of claim 1, wherein the multilayer seal is disposed within a gap between the lens of the device and the housing of the device.

16. The device of claim 1, wherein the multilayer seal is in contact with one or more of the entirety of a perimeter of the lens or the entirety of a perimeter of an aperture of the housing.

17. The device of claim 1, wherein the indicator material comprises a material that undergoes a color change after contacting a liquid.

18. The device of claim 17, wherein the liquid comprises one or more of a disinfectant or water.

19. The device of claim 1, wherein the ultrasound transducer is coupled to a proximal surface of the lens.

20. The device of claim 1, wherein the lens is an ultrasound acoustic lens.

21. The device of claim 1, wherein the ultrasound transducer comprises a microelectromechanical system (MEMS) array.

22. The device of claim 1, wherein the multilayer seal has a thickness from 1 μm to 1000 μm.

23. The device of claim 1, wherein the multilayer seal has a thickness that is constant.

24. The device of claim 1, wherein the multilayer seal has a thickness that is not constant.

25. The device of claim 1, wherein the first layer has a thickness from 1 μm to 125 μm.

26. The device of claim 1, wherein the first layer has a thickness that is constant.

27. The device of claim 1, wherein the first layer has a thickness that is not constant.

28. The device of claim 1, wherein the second layer has a thickness from 100 μm to 1000 μm.

29. The device of claim 1, wherein the second layer has a thickness less than 750 μm.

30. The device of claim 1, wherein the second layer has a thickness that is constant.

31. The device of claim 1, wherein the second layer has a thickness that is not constant.

32. The device of claim 1, wherein the multilayer seal has a width from 100 μm to 1000 μm.

33. The device of claim 1, wherein the second layer has a width that is constant.

34. The device of claim 1, wherein the second layer has a width that is not constant.

35. The device of claim 1, wherein the lens is coupled to the ultrasound transducer.

36. The device of claim 1, wherein the indicator material comprises an adhesive.

37. The device of claim 36, wherein the indicator material is adhered to one or more of a surface of the ultrasound transducer, a surface of an ASIC of the ultrasound device, or a surface of a MEMS wafer of the ultrasound device.

38. An ultrasound device comprising:
a housing;
a lens supported by the housing;
an ultrasound transducer disposed within the housing; and
a seal disposed between the housing and the lens, the seal comprising an indicator layer for detecting liquid intrusion and a sealant layer for preventing liquid intrusion, the sealant layer disposed distal to the indicator layer relative to the ultrasound transducer.

39. The ultrasound device of claim 38, wherein the seal is disposed within a gap between the lens and the housing.

40. The ultrasound device of claim 38, wherein the seal is in contact with one or more of the entirety of a perimeter of the lens or the entirety of a perimeter of an aperture of the housing.

41. The ultrasound device of claim 38, wherein the seal further comprises a secondary sealant layer disposed distal to the sealant layer relative to the ultrasound transducer.

42. The ultrasound device of claim 38, wherein the seal further comprises a secondary sealant layer disposed proximal to the sealant layer relative to the ultrasound transducer.

\* \* \* \* \*